US 6,561,986 B2

(12) United States Patent
Baura et al.

(10) Patent No.: US 6,561,986 B2
(45) Date of Patent: May 13, 2003

(54) METHOD AND APPARATUS FOR HEMODYNAMIC ASSESSMENT INCLUDING FIDUCIAL POINT DETECTION

(75) Inventors: Gail D. Baura, San Diego, CA (US); Sau Kuen Ng, San Diego, CA (US)

(73) Assignee: CardioDynamics International Corporation, San Diego, CA (US)

( * ) Notice: Subject to any disclaimer, the term of this patent is extended or adjusted under 35 U.S.C. 154(b) by 317 days.

(21) Appl. No.: 09/764,589

(22) Filed: Jan. 17, 2001

(65) Prior Publication Data

US 2002/0138014 A1 Sep. 26, 2002

(51) Int. Cl.⁷ ................................. A61B 5/02
(52) U.S. Cl. .................. 600/526; 600/536; 600/547
(58) Field of Search .................. 600/508, 509, 600/515, 516, 506, 526, 536, 546, 547; 607/27, 28, 32

(56) References Cited

U.S. PATENT DOCUMENTS

| RE30,101 E | 9/1979 | Kubicek et al. ............ 600/526 |
|---|---|---|
| 4,802,491 A | 2/1989 | Cohen et al. ................ 600/515 |
| 5,010,888 A | 4/1991 | Jadvar et al. ............... 600/509 |
| 5,178,154 A * | 1/1993 | Ackmann et al. ........... 600/526 |
| 5,277,189 A | 1/1994 | Jacobs ........................ 600/508 |
| 5,309,917 A | 5/1994 | Wang et al. ................. 600/508 |
| 5,311,874 A | 5/1994 | Baumann et al. ........... 600/518 |
| 5,391,199 A | 2/1995 | Ben-Haim .................. 607/122 |
| 5,423,326 A | 6/1995 | Wang et al. ................. 600/526 |
| 5,439,483 A | 8/1995 | Duong-Van .................... 607/5 |
| 5,443,073 A | 8/1995 | Wang et al. ................. 600/526 |
| 5,505,209 A | 4/1996 | Reining ...................... 600/547 |
| 5,546,951 A | 8/1996 | Ben-Haim .................. 600/515 |
| 5,730,142 A | 3/1998 | Sun et al. ................... 600/578 |
| 5,778,881 A | 7/1998 | Sun et al. ................... 600/509 |
| 5,782,888 A | 7/1998 | Sun et al. ..................... 607/27 |
| 5,895,298 A | 4/1999 | Faupel et al. ............... 439/729 |
| 5,902,325 A * | 5/1999 | Condie et al. ................ 607/28 |
| 5,913,826 A | 6/1999 | Blank .......................... 600/500 |
| 5,967,995 A | 10/1999 | Shusterman et al. ........ 600/516 |
| 6,022,322 A * | 2/2000 | Prutchi ....................... 600/506 |
| 6,115,628 A | 9/2000 | Stadler et al. .............. 600/517 |
| 6,128,526 A | 10/2000 | Stadler et al. .............. 600/517 |
| 6,186,955 B1 | 2/2001 | Baura ......................... 600/526 |
| 6,370,424 B1 * | 4/2002 | Prutchi ....................... 600/536 |

OTHER PUBLICATIONS

Nyboer, Jan, Sc.D. , M.D., et al., (1950), "Electrical Impedance Plethysmography," Circulation, vol. II, pp. 811–821.

Kubicek, W.G., et al., (1966), "Development and Evaluation of An Impedance Cardiac Output System," Aerospace Med., 37:1208–1212.

Lababidi, Z., et al., (1970) "The First Derivative Thoracic Impedance Cardiogram," Circulation, 41:651–658.

(List continued on next page.)

Primary Examiner—Willis R. Wolfe
(74) Attorney, Agent, or Firm—Gazdzinski & Associates

(57) ABSTRACT

An improved method and apparatus for non-invasively assessing one or more hemodynamic parameters associated with the circulatory system of a living organism. In one exemplary embodiment, the invention comprises a method of measuring cardiac output (CO) using impedance waveforms (and ECG waveforms) which are analyzed via discrete wavelet transforms. These transforms aid in identifying fiducial points within the waveforms, the fiducial points being used to calculate various parameters relating to cardiac stroke volume (such as LVET and $dZ/dt_{max}$), from which cardiac output may be determined. The use of wavelet transforms for fiducial point detection increases the accuracy of the CO determination by reducing cross-term artifact, and also significantly reduces the amount and complexity of processing required as compared to prior art time-frequency distribution or empirical techniques. Improved methods of QRS complex detection within the ECG waveform, and median filtering of an input waveform, are also disclosed.

46 Claims, 14 Drawing Sheets

OTHER PUBLICATIONS

Sramek, B.B., (1982), "Cardiac Output by Electrical Impedance," Med. Elect, 13:93–97.

Bernstein, D.P., (1986), "A New Stroke Volume Equation for Thoracic Electrical Bioimpedance: Theory and Rationale," Critical Care Med., 14:904–909.

Li, C., et al., (1995), "Detection of ECG Characteristic Points Using Wavelet Transforms," IEEE Trans. BME, vol. 42, No. 1, pp. 21–28.

Kadambe, S., et al., (1995), "Wavelet Transform–Based QRS Complex Detector," IEEE Trans. BME, vol. 46, No. 7, pp. 838–848.

Newman, D.G., et al., (1999), "The Non–Invasive Assessment of Stroke Volume and Cardiac Output by Impedance Cardiography: A Review," Aviation, Space, and Environmental Medicine, vol. 70, No. 8, pp. 780–789.

Afonso, V. X., et al., (1999), "ECG Beat Detection Using Filter Banks," IEEE Trans. BME, vol. 46, No. 2, pp. 838–848.

Application Ser. No. 09/613,183 entitled "Apparatus and Method for Determining Cardiac Output in a Living Subject," filed Jul. 10, 2000—Attorney Docket No. CARDIO.003A.

* cited by examiner

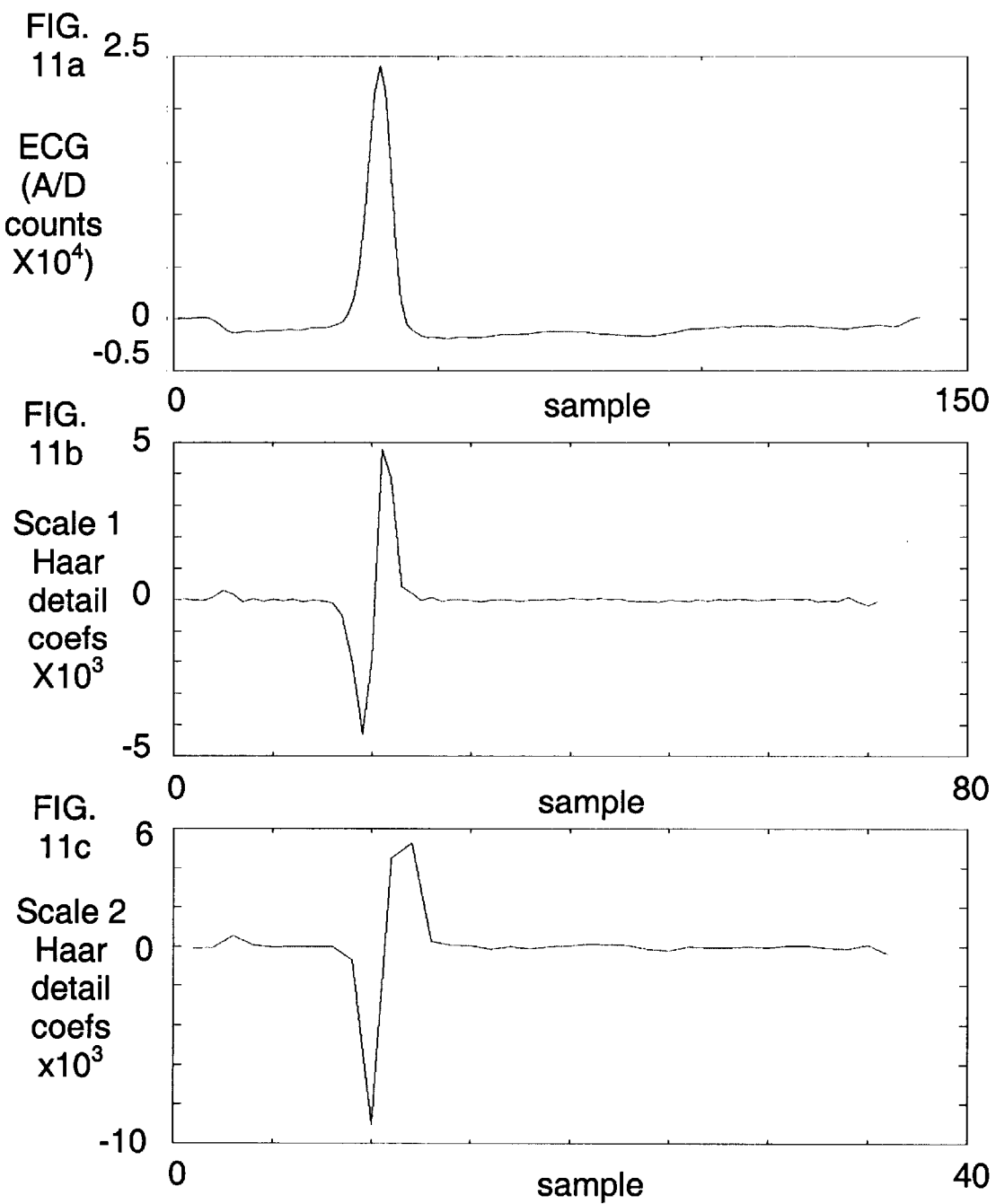

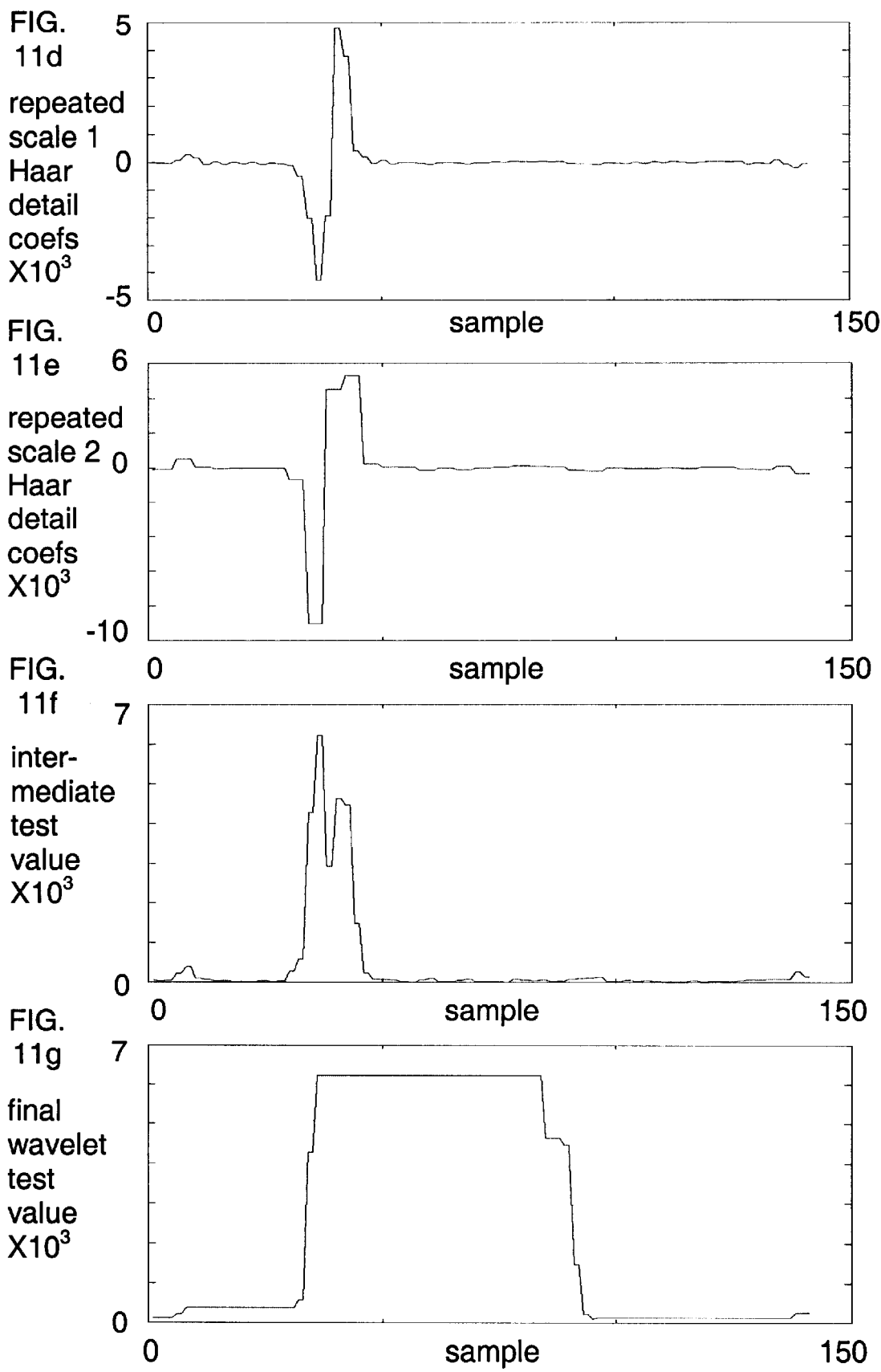

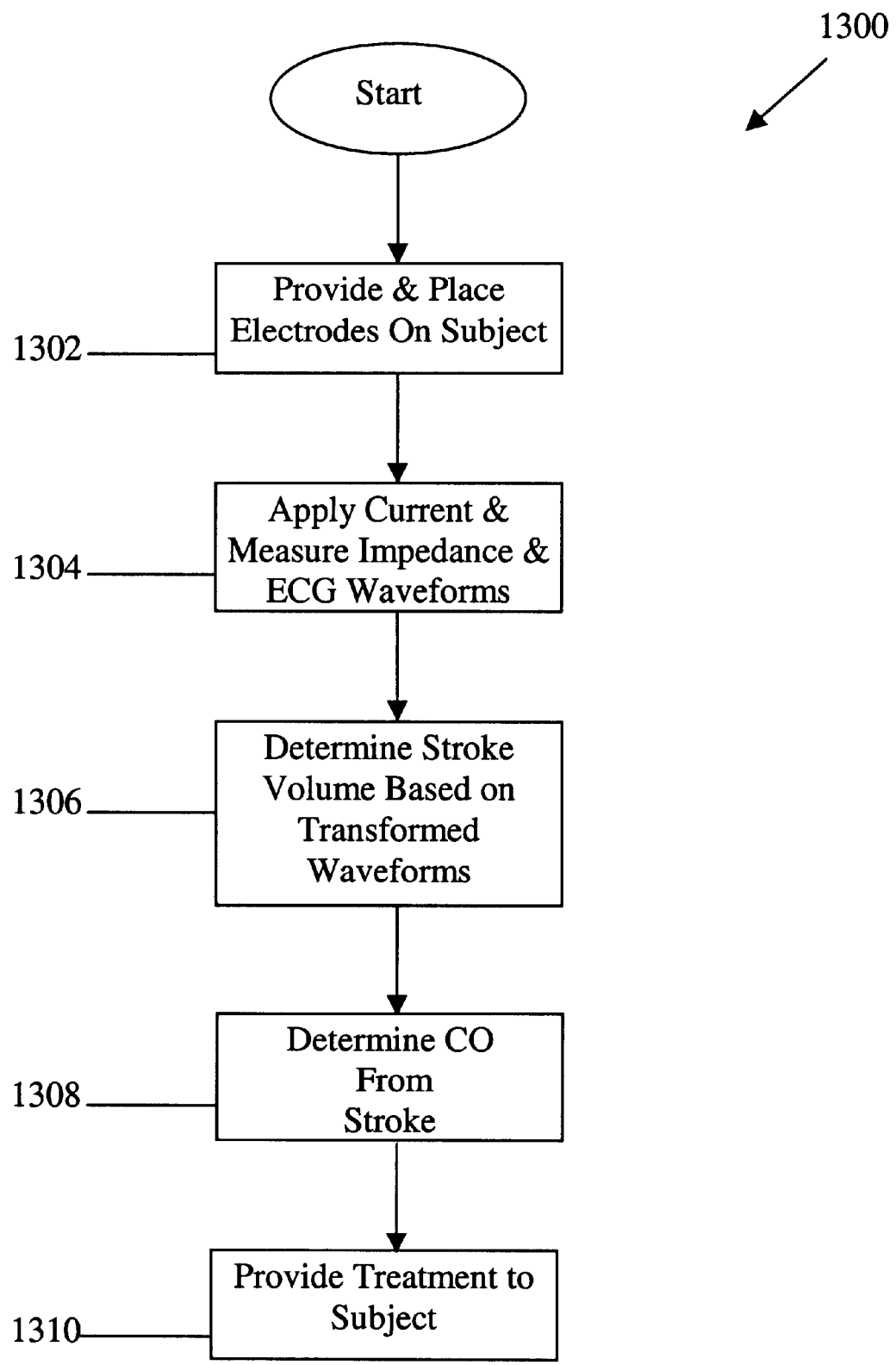

METHOD AND APPARATUS FOR HEMODYNAMIC ASSESSMENT INCLUDING FIDUCIAL POINT DETECTION

BACKGROUND OF THE INVENTION

1. Field of the Invention

This invention relates generally to the field of hemodynamic analysis of living subjects, and particularly to an apparatus and method for non-invasively detecting and evaluating fiducial points within waveforms such as those present in the impedance cardiograms and electrocardiograms of the subject.

2. Description of Related Technology

The study of the performance and properties of the cardiovascular system of a living subject has proven useful for diagnosing and assessing any number of conditions or diseases within the subject. The performance of the cardiovascular system, including the heart, has characteristically been measured in terms of several different parameters, including the stroke volume and cardiac output of the heart.

Noninvasive estimates of cardiac output (CO) can be obtained using the well known technique of impedance cardiography (ICG). Strictly speaking, impedance cardiography, also known as thoracic bioimpedance or impedance plethysmography, is used to measure the stroke volume (SV) of the heart. As shown in Eqn. (1), when the stroke volume is multiplied by heart rate, cardiac output is obtained.

$$CO = SV \times \text{heart rate.} \quad \text{(Eqn. 1)}$$

During impedance cardiography, a constant alternating current, with a frequency such as 70 kHz, I(t), is applied across the thorax. The resulting voltage, V(t), is used to calculate impedance. Because the impedance is assumed to be purely resistive, the total impedance, $Z_T(t)$, is calculated by Ohm's Law. The total impedance consists generally of a constant base impedance, $Z_o$, and time-varying impedance, $Z_c(t)$, as shown in Eqn. 2:

$$Z_T(t) = \frac{V(t)}{I(t)} = Z_o + Z_c(t). \quad \text{(Eqn. 2)}$$

The time-varying impedance is believed to reflect the change in blood resistivity as it transverses through the aorta.

Stroke volume is typically calculated from one of three well known equations, based on this impedance change:

$$\text{Kubicek:} \quad SV = \rho\left(\frac{L^2}{Z_o^2}\right) LVET \frac{dZ(t)}{dt_{\max}}, \quad \text{(Eqn. 3)}$$

$$\text{Sramek:} \quad SV = \frac{L^3}{4.25 Z_o} LVET \frac{dZ(t)}{dt_{\max}}, \quad \text{(Eqn. 4)}$$

$$\text{Sramek-Bernstein:} \quad SV = \delta \frac{(0.17H)^3}{4.25 Z_o} LVET \frac{dZ(t)}{dt_{\max}}. \quad \text{(Eqn. 5)}$$

Where:

L=distance between the inner electrodes in cm,
LVET=ventricular ejection time in seconds,
$Z_o$=base impedance in ohms, $\frac{dZ(t)}{dt_{\max}}$ = magnitude of the largest negative derivative of the impedance change, $Z_c(t)$, occurring during systole in ohms/s,
ρ=resistivity of blood in ohms-cm,
H=subject height in cm, and
δ=special weight correction factor.

Two key parameters present in Eqns. 3, 4, and 5 above are (i)

$$\frac{dZ(t)}{dt_{\max}}$$

and (ii) LVET. These parameters are found from features referred to as fiducial points, that are present in the inverted first derivative of the impedance waveform, $$\frac{dZ(t)}{dt}.$$

As described by Lababidi, Z., et al, "The first derivative thoracic impedance cardiogram," Circulation, 41:651–658, 1970, the value of $$\frac{dZ(t)}{dt_{\max}}$$

is generally determined from the time at which the inverted derivative value has the highest amplitude, also commonly referred to as the "C point". The value of $$\frac{dZ(k)}{dt_{\max}}$$

is calculated as this amplitude value. LVET corresponds generally to the time during which the aortic valve is open. That point in time associated with aortic valve opening, also commonly known as the "B point", is generally determined as the time associated with the onset of the rapid upstroke (a slight inflection) in $$\frac{dZ(t)}{dt}$$

before the occurrence of the C point. The time associated with aortic valve closing, also known as the "X point", is generally determined as the time associated with the inverted derivative global minimum, which occurs after the C point, as illustrated in FIG. 1.

In addition to the foregoing "B", "C", and "X" points, the so-called "O point" may be of utility in the analysis of the cardiac muscle. The O point represents the time of opening of the mitral valve of the heart. The O point is generally determined as the time associated with the first peak after the X point. The time difference between aortic valve closing and mitral valve opening is known as the isovolumetric relaxation time, IVRT. However, to date, the O point has not found substantial utility in the stroke volume calculation.

Impedance cardiography further requires recording of the subject's electrocardiogram (ECG) in conjunction with the thoracic impedance waveform previously described. Processing of the impedance waveform for hemodynamic analysis requires the use of ECG fiducial points as landmarks. Processing of the impedance waveform is generally performed on a beat-by-beat basis, with the ECG being used for beat detection. In addition, detection of some fiducial points of the impedance signal may require the use of ECG fiducial points as landmarks. Specifically, individual beats are identified by detecting the presence of QRS complexes within the ECG. The peak of the R wave (commonly referred to as the "R point") in the QRS complex is also detected, as well as the onset of depolarization of the QRS complex ("Q point").

Historically, the aforementioned fiducial points in the impedance cardiography waveform (i.e., B, C, O, and X points) and ECG (i.e. R and Q points) were each determined through empirical curve fitting. However, such empirical curve fitting is not only labor intensive and subject to several potential sources of error, but, in the case of the impedance waveform, also requires elimination of respiratory artifact. More recently, digital signal processing has been applied to the impedance cardiography waveform for pattern recognition. One mathematical technique used in conjunction with such processing, the well known time-frequency distribution, utilizes complex mathematics and a well known time-frequency distribution (e.g., the spectrogram). See for example, U.S. Pat. Nos. 5,309,917, 5,423,326, and 5,443,073 issued May 10, 1994, Jun. 13, 1995, and Aug. 22, 1995, respectively, and assigned to Drexel University. As discussed in the foregoing patents, the spectrogram is used for extraction of information relating to the transient behavior of the dZ/dt signal. Specifically, a mixed time-frequency representation of the signal is generated through calculation of the Fast Fourier Transform and multiplication by a windowing function (e.g., Hamming function) to convert the one-dimensional discrete dZ/dt signal into a two-dimensional function with a time variable and frequency variable.

However, the spectrogram (and many of the time-frequency distributions in general) suffers from a significant disability relating to the introduction of cross term artifact into the pattern recognition calculations. Specifically, when a signal is decomposed, the time-frequency plane should accurately reflect this signal. If a signal is turned off for a finite time, some time-frequency distributions will not be zero during this time, due to the existence of interference cross terms inherent in the calculation of the distribution.

Another limitation of the spectrogram is its assumption of stationarity within the windowing function. This assumption is valid if the frequency components are constant throughout the window. However, biological signals, including the ECG and the impedance waveform, are known to be non-stationary.

Additionally, the signal processing associated with such time-frequency distributions by necessity incorporates complex mathematics (i.e., involves operands having both real and imaginary components), which significantly complicates even simple pattern recognition-related computations.

Furthermore, such prior art empirical and time-frequency processing techniques impose substantial filtering requirements which can be restrictive in terms of hardware implementation. For example, the time delay associated with ΔZ waveforms may be large due to factors such as sharp frequency cutoffs required for empirical fiducial point detection.

Based on the foregoing, what is needed is an improved method and apparatus for assessing hemodynamic parameters, including cardiac output, within a living subject.

Such method and apparatus would ideally be completely non-invasive, accurate, easily adapted to the varying physiology of different subjects, and would produce reliable results under a variety of different operating conditions. Additionally, such improved method and apparatus would be based on comparatively simple mathematical operations and non-imaginary operands, thereby reducing the burden on associated signal processing hardware and software. Ideally, the effects of other potential sources of error (such as respiratory artifact) would also be mitigated or eliminated.

SUMMARY OF THE INVENTION

The present invention satisfies the aforementioned needs by an improved method and apparatus for non-invasively assessing hemodynamic parameters, including cardiac output, within a living subject.

In a first aspect of the invention, an improved method of determining at least one hemodynamic parameter associated with a living subject is disclosed. In one exemplary embodiment, the hemodynamic parameter comprises cardiac output, and the method comprises providing a plurality of electrodes disposed relative to the thoracic cavity of the subject; measuring at least one impedance waveform associated with the thoracic cavity using at least one of the plurality of electrodes; processing at least one impedance waveform using wavelet transforms to identify one or more fiducial points within the impedance waveform; and determining cardiac output based at least in part on the one or more fiducial points. Rather than using prior art empirical curve fitting or time-frequency distributions, the fiducial points of the ΔZ and dZ/dt waveforms (e.g., B, C, X, and O) are detected in the present invention using discrete wavelet transforms. The difference between each detected X and B point is used in the present embodiment to calculate ventricular ejection time (LVET). The magnitude of the largest negative derivative of the impedance change occurring during systole ($dZ/dt_{max}$) is calculated from the C point. LVET and $dZ/dt_{max}$ are then used to calculate the stroke volume, from which cardiac output is derived.

In contrast to the extensive processing and complex mathematics associated with the prior art time-frequency method, the wavelet transform methodology of the present invention advantageously requires only simple additions and multiplications of real numbers, thereby substantially simplifying the processing associated with the cardiac output (CO) determination. Furthermore, cross terms are minimized as part of the wavelet transform methodology of the present invention, thereby increasing the accuracy of the CO determination.

In a second aspect of the invention, a method of detecting specific events within a second hemodynamic parametric waveform is disclosed. In one exemplary embodiment, the second waveform comprises the electrocardiogram (ECG) of the subject, the specific events comprise individual "beats" of the subject's cardiac muscle, and the method comprises measuring at least one ECG waveform using at least one of the plurality of electrodes; processing the at least one waveform using discrete wavelet transforms to identify one or more fiducial points within the ECG; identifying one or more QRS complexes based at least in part on the one or more fiducial points; and identifying beats based at least in part on the identified QRS complex(es). The peak of the R wave (R point) in the QRS complex as well as the onset of depolarization of the QRS complex (Q point) are also detected. The time interval between the R waves is also used to calculate the heart rate.

In a third aspect of the invention, an improved computer program for implementing the aforementioned methods of hemodynamic parametric assessment (e.g., determination of cardiac output from the impedance waveform, and identification of cardiac beats within the ECG) using discrete wavelet transforms is disclosed. In a first exemplary embodiment, the computer program comprises an object code representation of an assembly language source code listing, the object code representation being disposed on a transportable storage medium (e.g., floppy disk). In a second embodiment, the computer program is disposed on the discrete storage device of a signal processing apparatus and adapted to run on the digital processor thereof. The computer program further comprises a graphical user interface (GUI) operatively coupled to the display and input device of the signal processing apparatus. One or more subroutines or algorithms for implementing the discrete wavelet transform and fiducial point detection methodologies of the invention are included within the program. In a third exemplary embodiment, the computer program comprises an instruction set disposed within the storage device (such as the embedded program memory) of the digital signal processor (DSP) of the signal processing apparatus.

In a fourth aspect of the invention, an improved apparatus for assessing one or more hemodynamic parameters associated with a living subject is disclosed. In one exemplary embodiment, the hemodynamic parameter under evaluation comprises the cardiac output of the subject, and the apparatus generally comprises a plurality of electrodes disposed in proximity to the thoracic cavity of the subject; a current source adapted to provide a predetermined current through the thoracic cavity of the subject via at least one of the plurality of electrodes; and a signal processing apparatus adapted to analyze the signals obtained from the electrodes and determine stroke volume (and accordingly cardiac output) therefrom. The signal processing apparatus comprises a signal conditioning apparatus adapted to process signals (including the impedance signal(s) and ECG derived from one or more of the electrodes) and produce conditioned signals relating thereto; and a processor adapted to detect the fiducial points within the impedance signal(s) or conditioned signals using discrete wavelet transforms, from which cardiac output is ultimately determined.

In one variant, the apparatus further comprises an analog-to-digital converter which converts the analog signals to a binary digital format for use by the processor, the processor comprising a digital signal processor (DSP) adapted to run one or more of the aforementioned fiducial point detection computer programs thereon. The apparatus also includes a random access memory (RAM) or other storage device in data communication with the processor for storing data prior to and/or after processing by the processor.

In a fifth aspect of the invention, an improved method of providing treatment to a subject using the aforementioned cardiac output assessment methodology is disclosed. The method generally comprises the steps of: disposing a plurality of electrodes with respect to the thoracic cavity of the subject; measuring the impedance and ECG data of the subject non-invasively; determining the stroke volume of the subject's cardiac muscle during at least one cardiac cycle using discrete wavelet transforms; determining the cardiac output of the subject based at least in part on the stroke volume, and providing treatment to the subject based on the determined cardiac output.

BRIEF DESCRIPTION OF THE DRAWINGS

FIG. 11a is a graph of an exemplary ECG waveform obtained from a living subject.

FIG. 11b is a graph of exemplary detail coefficients at scale 1, $Y_{s1}$, obtained from the ECG waveform of FIG. 11a.

FIG. 11c is a graph of exemplary detail coefficients at scale 2, $Y_{s2}$, obtained from the ECG waveform of FIG. 11a.

FIG. 11d is a graph of exemplary repeated detail coefficients at scale 1, $WT_{s1}$ obtained from the ECG waveform of FIG. 11a.

FIG. 11e is a graph of exemplary repeated detail coefficients at scale 2, $WT_{s2}$, obtained from the ECG waveform of FIG. 11a.

FIG. 11f is a graph of exemplary intermediate test values, $w_T$, obtained from the ECG waveform of FIG. 11a.

FIG. 11g is a graph of exemplary wavelet test values, $w_T$, obtained from the ECG waveform of FIG. 11a.

FIG. 13 is a logical flow diagram illustrating one exemplary embodiment of the method of providing treatment to a subject using the aforementioned methods.

DETAILED DESCRIPTION OF THE INVENTION

Reference is now made to the drawings wherein like numerals refer to like parts throughout.

It is noted that while the invention is described herein in terms of an apparatus and method for determining cardiac output suitable for use on the thorax of a human subject, the invention may also be embodied or adapted to monitor cardiac output at other locations on the human body, as well as monitoring cardiac output on other warm-blooded species such as, for example, primates, canines, or porcines. All such adaptations and alternate embodiments are considered to fall within the scope of the claims appended hereto.

I. Overview

In one fundamental aspect, the present invention comprises a method of assessing hemodynamic parameters within a living subject through analysis of signals relating to the subject's physiology using discrete wavelet transforms. For example, as will be described in greater detail below, the present invention is useful in accurately and non-invasively determining the stroke volume associated with the cardiac cycle of the subject, thereby advantageously allowing the accurate determination of the subject's cardiac output (CO). The QRS complex(es) present in the subject's ECG waveform are also detected using discrete wavelet transforms.

Figure 2:
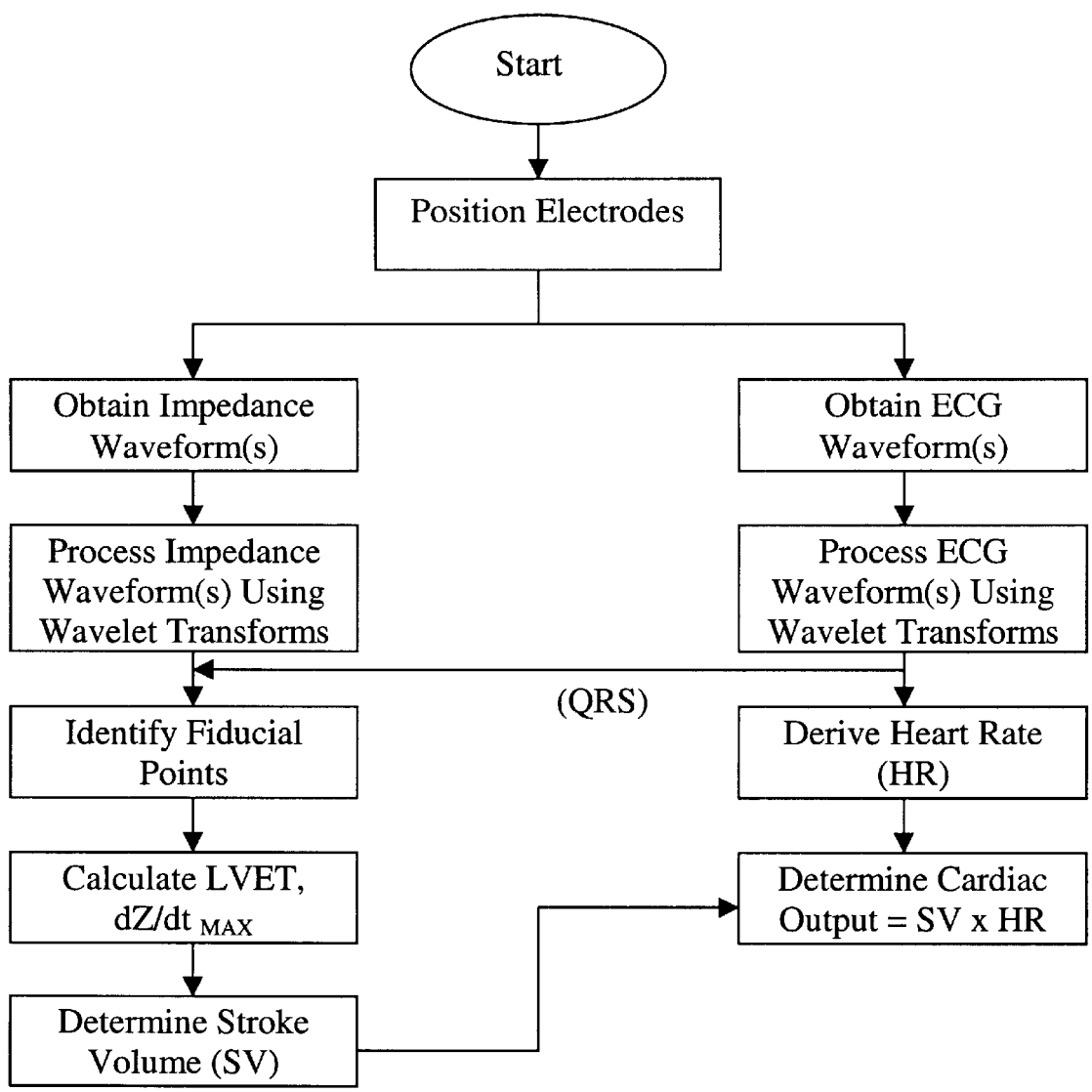
FIG. 2 is a logical flow diagram illustrating one exemplary embodiment of the waveform analysis methodology of the present invention in the context of a cardiac output (CO) determination.

A discrete wavelet transform is a time-scale representation of an input signal that is obtained by convolving the signal with a wavelet or scaling filter at a particular scale. Various wavelet and scaling filters are utilized as part of the invention to emphasize certain features of interest associated with the input impedance and ECG waveforms obtained from electrodes positioned on the subject's thorax. The resulting emphasized feature in each wavelet transform is then detected to obtain a fiducial point (e.g., B, C, O, X for the impedance waveform, and Q or R for the ECG waveform). The difference between each detected X and B point in the impedance waveform is used to calculate ventricular ejection time (LVET), and $dZ/dt_{max}$ is calculated from the C point. LVET and $dZ/dt_{max}$ are then used to calculate the stroke volume. The stroke volume is then multiplied by the heart rate, which is determined from detection of the R point, to estimate CO. This general methodology is illustrated graphically in FIG. 2.

In order to simplify fiducial point detection within the waveforms, the fiducial points are detected in the present invention on a "per-beat" basis (as opposed to over several beats). Each individual beat under consideration is divided by its Q points, where a Q point is equivalent to the start of the Q wave of the electrocardiogram QRS complex.

Table 1 below provides a summarization of the foregoing parameters related to cardiac output determination and QRS complex detection as used in relation to the present invention.

TABLE 1

| | |
|---|---|
| B point | Sample signifying initial aortic valve opening. |
| C point | Sample during which dZ/dt is maximum. |
| ΔZ | Time-varying portion of the impedance signal, which is commonly inverted before further processing. |
| dZ/dt | First derivative of the impedance signal. |
| $dZ/dt_{max}$ | Maximum value of the first derivative of the impedance signal. |
| LVET | Left ventricular ejection time, which is the time interval during which the aortic valve is open. |
| O point | Sample during which the mitral valve opens. |
| Q point | Sample signifying initial ventricular depolarization. |
| R point | Sample signifying maximum deflection in QRS complex. |
| Sample, k | Digitized time. |
| X point | Sample during which the aortic valve closes. |

Use of the discrete wavelet transform of the present invention advantageously (i) reduces the so-called "cross-term artifact" previously described with respect to the prior art time-frequency distribution approach, thereby increasing accuracy; (ii) is better suited for non-stationary signals, thereby localizing the fiducial points in time with more accuracy, and (iii) greatly simplifies the requisite processing associated with the SV and CO determinations, thereby increasing the speed of the computation, or conversely allowing the use of a reduced processor clock frequency or a lower MIPS device. The benefits of (iii) are especially useful in reducing the complexity and cost of the apparatus used to measure CO, as well as reducing the power consumption of the device and increasing battery longevity (such as in the case of a portable or hand-held unit).

It will be recognized, however, that while exemplary embodiments of apparatus and methodology are described herein in terms of the cardiac output determination, the invention also be readily used in assessing other hemodynamic parameters, such as the pre-ejection period (PEP, the interval between Q point and B point), isovolumetric relaxation time, presence of excess intravascular fluid, presence of excess pulmonary fluid and the like, and accordingly is not limited to the measurement of stroke volume, cardiac output, or QRS complex identification.

II. Impedance Waveform Analysis

Figure 3:
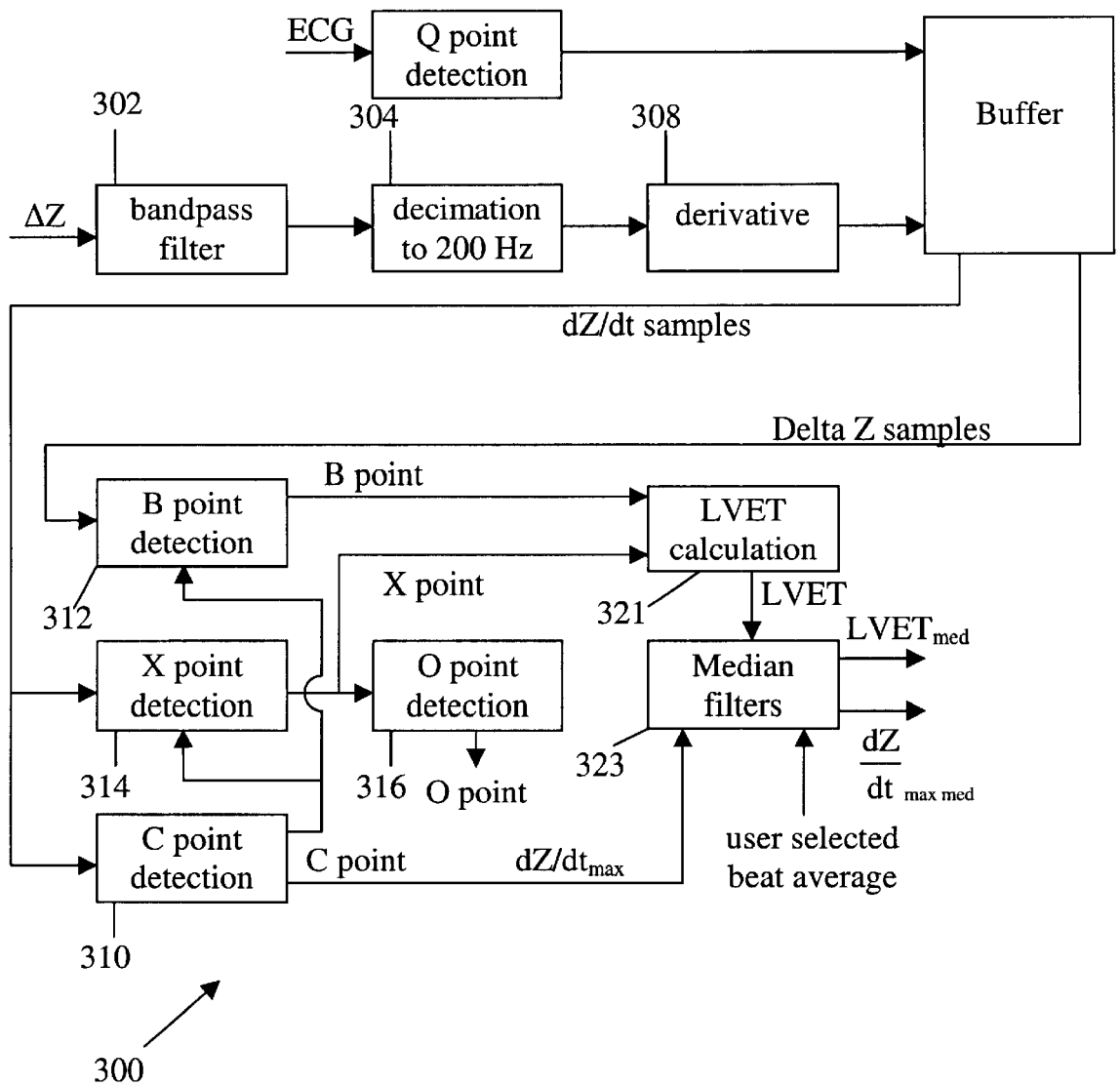
FIG. 3 is a logical flow diagram illustrating the methodology of FIG. 2 in greater detail, including pre-processing and fiducial point detection.

Referring now to FIG. 3, the method 300 processing of the impedance (Z) signal(s) obtained from the living subject to determine cardiac output is described in greater detail. As shown in FIG. 3, the ΔZ waveform is first bandpass filtered (step 302) and decimated (step 304). This produces a 200 Hz waveform, although it will be recognized that other nominal frequencies may be substituted. The time derivative of impedance, dZ/dt, is calculated per step 308, using 40 msec differences, although other time difference increments may be used as desired. The range of samples of ΔZ and dZ/dt that are used for B, C, X, and O detection are identified as those samples between the two most recently detected Q points. This range is defined as shown in Eqn. 6:

$$\{\text{first Q point, (second Q point}-1)\} \tag{Eqn. 6}$$

Figure 1:
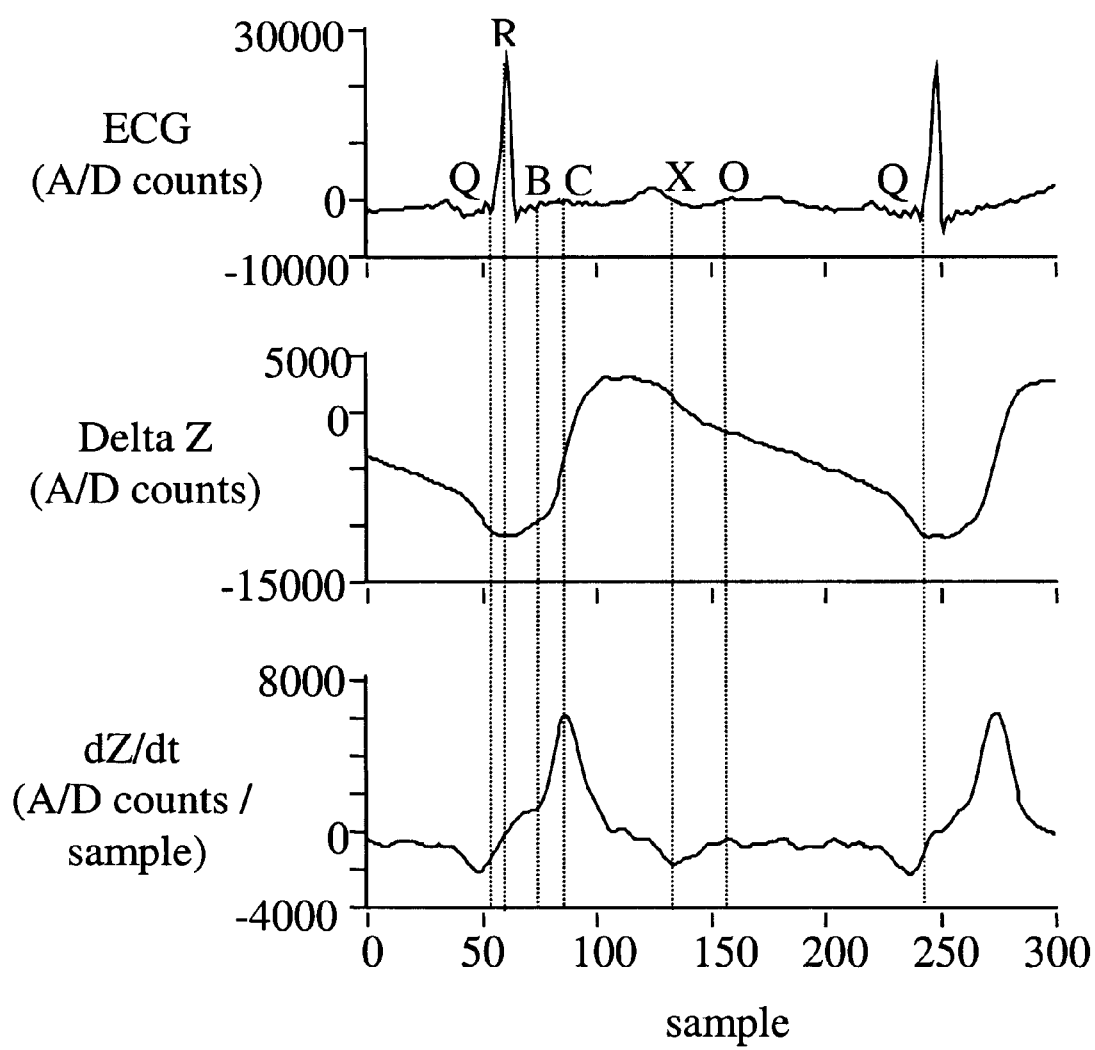
FIG. 1 is a graphical representation of the ECG, $\Delta Z$ and $dZ/dt$ waveforms obtained from a typical living subject, illustrating the relative disposition of the various fiducial points therein.

Based on an exemplary human physiology, the typical order of occurrence of the fiducial points (with increasing time) is: (i) the first Q point, (ii) R point, (iii) B point, (iv) C point, (v) X point, (vi) O point, and (vii) the second Q point, as illustrated in FIG. 1. It can generally be assumed that the B point follows the R point, where the R point is equivalent to the maximum deflection of the R wave of the electrocardiogram QRS complex. Accurate Q point detection of the ECG is important because it affects the fiducial point detection of the impedance waveform, and is also used in the calculation of the pre-ejection period. Detection of the QRS complex, and the Q and R points, is discussed in detail below with respect to FIGS. 10–11g.

Because the C point is generally the simplest to detect, this point is detected first per step 310 of FIG. 3. The B point is then detected in step 312 from the sample range defined by {R point, C point}. The X point is detected in step 314 from the sample range defined by {C point, second Q point−1}. After X point detection, the O point is detected from the sample range {X point, (second Q point−1)} in step 316.

The C point is generally identified as the sample with the highest dZ/dt amplitude. However, in the case of volume loaded patients (i.e., those with increased intravascular volume such as hemodialysis patients immediately before scheduled dialysis), when two such characteristic peaks are present in the dZ/dt waveform, the C point is the sample associated with the first occurring peak. This relationship is illustrated in FIG. 4.

The B point is generally identified as the sample associated with the onset of the rapid upstroke (a slight inflection) in dZ/dt before the occurrence of the C point. This inflection is created by a local minimum in ΔZ that occurs near the beginning of the ΔZ period, as illustrated in FIG. 4. The X point is generally identified as the sample associated with the global minimum, which occurs after the C point. As used herein, the term "global minimum" refers to the minimum value within a given range of samples. However, the global minimum may occur after the O point, as shown in FIG. 1. Therefore, in the context of the present embodiment, the X point is the first "significant" local minimum that occurs after the C point, although other definitions may be applied.

Figure 4:
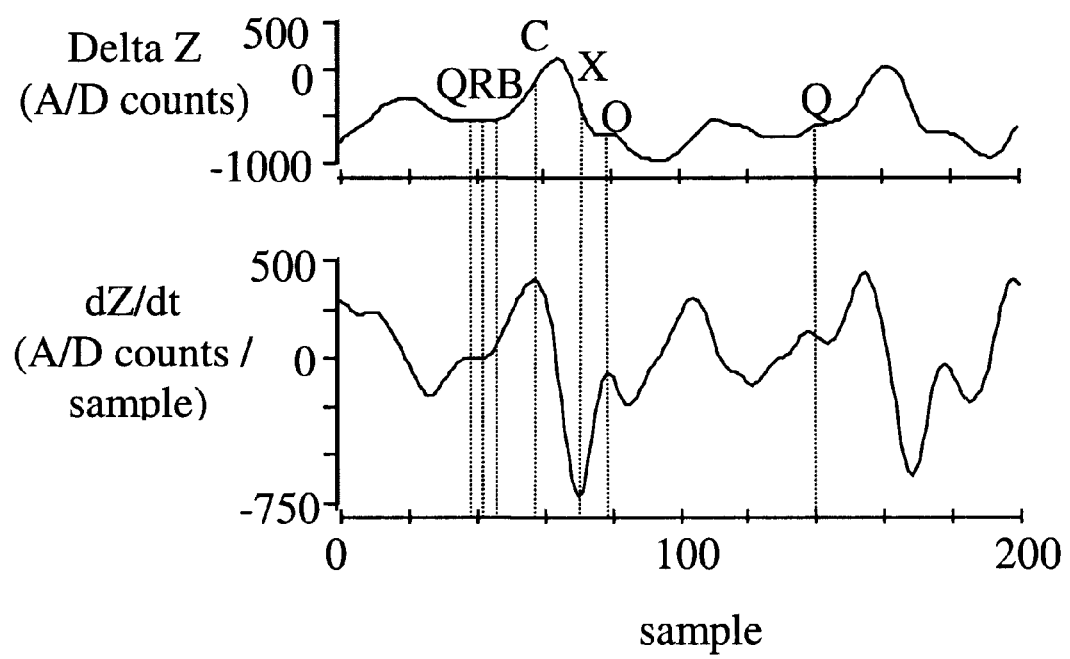
FIG. 4 is a graphical representation illustrating fiducial point detection in the impedance waveform of a volume loaded patient.

The O point is generally identified as the sample associated with the first peak after the X point, as illustrated in FIGS. 1 and 4.

On a per beat basis, the difference between each detected X and B point is used to calculate LVET (step 321 of FIG. 3). On a per beat basis, $dZ/dt_{max}$ is calculated from the C point per step 323.

Wavelet Transforms

As previously discussed, the fiducial points associated with the impedance waveforms (and ECG waveforms, described in detail below) are detected in the present invention using discrete wavelet transforms. As is generally known, a discrete wavelet transform is a time-scale representation of an input signal that is obtained by filtering the signal with a wavelet transform pair at a particular scale, j The wavelet transform pair is composed of a scaling filter and wavelet filter. The scaling filter, $\phi_A(k)$, acts as a lowpass filter, of the type known in the art to obtain wavelet transform approximation coefficients The wavelet filter, $\psi_D(k)$, acts as a highpass filter to obtain wavelet transform detail coefficients. For calculations at scale j, note that the input signal, WT(k, j−1), is either a waveform signal at scale 0, x(k), or approximation coefficients at scale (j−1). The output approximation or detail coefficients, WT(k,j), may be calculated using Eqn. 7.

$$WT(k, j) = \sum_{i=0}^{L-1} WT(i, j-1)g(2k-i) \quad \text{(Eqn. 7)}$$

where:

k=sample,

L=length of the input signal, and g(k) is the wavelet or scaling filter.

Eqn. 7 provides the basis for the wavelet transform calculations of the present embodiment. In general, the present invention advantageously utilizes various wavelet and scaling filters (described in greater detail below) to emphasize certain features of an input signal. The resulting features in wavelet transform approximation or detail coefficients are then detected to obtain one or more fiducial points associated with the input waveform(s). This process 500 is illustrated graphically in FIG. 5.

Fiducial Point Detection

Figure 6:
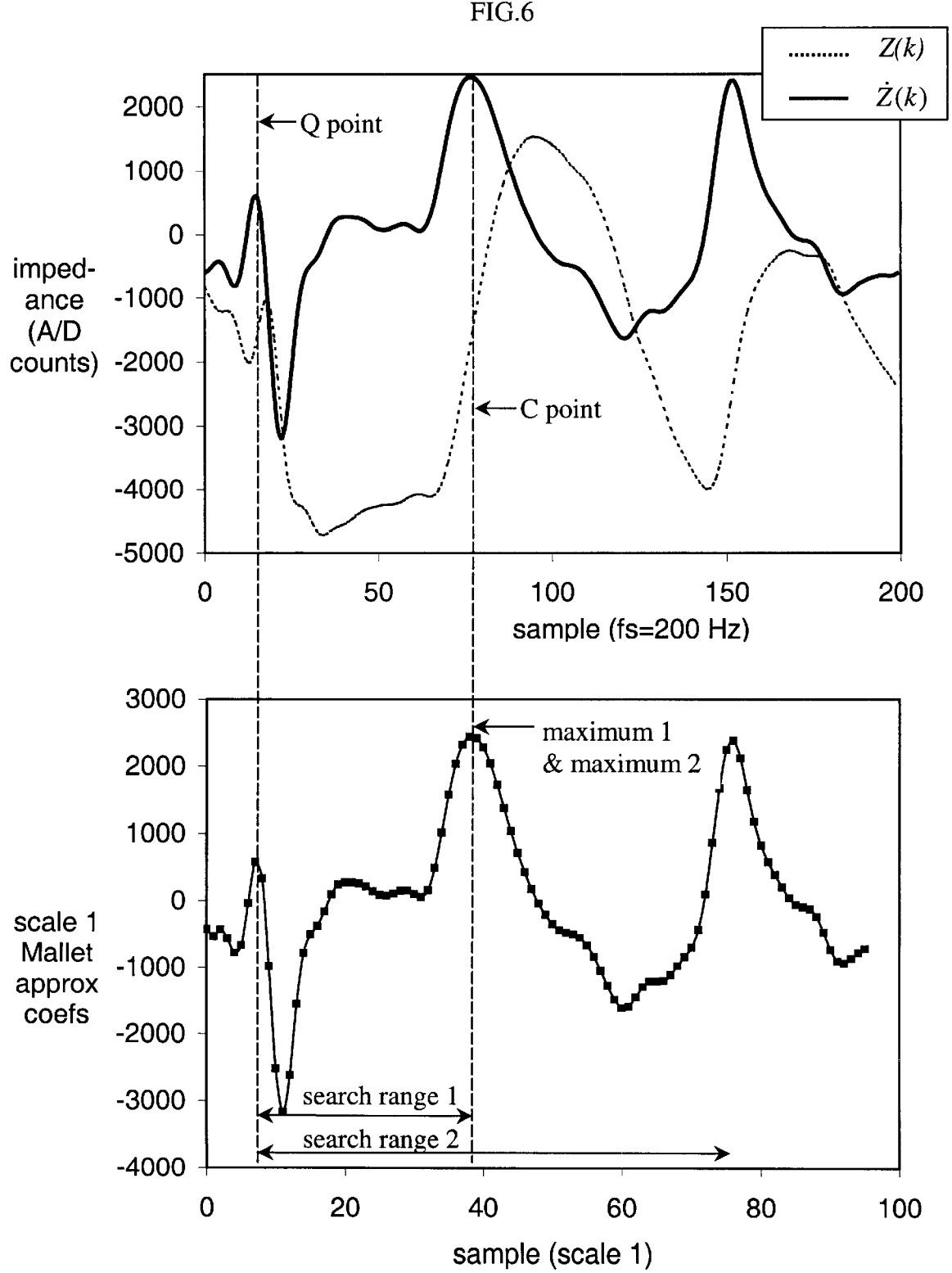
FIG. 6 is a graph illustrating exemplary C point detection using the Mallet scaling filter, $m_A(k)$, according to the invention, acquired from a 62 year old, 82 kg male pacemaker patient.

According to the present embodiment of the invention, the C point of the impedance waveform is detected (step 310 of FIG. 3) from scale 1 approximation coefficients of dZ/dt, based on the Mallet scaling filter, as illustrated in FIG. 6. The Mallet scaling filter, $m_A(k)$, may be defined as shown in Eqn. 8 below:

$m_A(k)$={−0.0132, −0.0393, −0.0450, 0.2864, 0.4347, 0.2864, 0.0450, −0.0393, −0.0132} (Eqn. 8)

The C point is further detected within the sample range k={first Q point, (second Q point−1)}. Based on previous ECG detection processing (discussed below), k=0 is set to equal the first Q point.

It will be recognized that while the following discussion of the wavelet transform and fiducial point detection methodologies of the invention is cast in terms of sets of input, internal, and output parameters associated with an exemplary set of algorithms (e.g., computer program) used for analyzing the impedance and ECG waveforms in conjunction with a digital signal processing device, such parameters are merely illustrative of the broader analytical methods involved. Accordingly, a variety of different approaches may be used to achieve the objective of identifying fiducial points and/or artifacts present in the waveforms using discrete wavelet transforms. For example, it is possible to reduce portions or even all of the calculations set forth below to dedicated circuitry, such as might be fabricated on an application specific integrated circuit (ASIC), or even as discrete analog circuits or components. All such alternative approaches are considered to be within the scope of the claims appended hereto.

The following input parameters are utilized as part of the exemplary C point detection algorithm of the present embodiment:

1. dZ/dt(k)=The first derivative of the impedance signal.
2. Length, L=The total number of samples within the current Q-Q interval.

Similarly, the following exemplary internal parameters (i.e., intermediate calculations using input parameters to obtain the output) are utilized in C point detection according to the present embodiment:

i. Max1=The sample associated with the global maximum scale 1 approximation coefficient within the range k={0, [(L−1)/6]}.
ii. Max2=The sample associated with the global maximum scale 1 approximation coefficient within the range k={0, [(L−1)/4]}.
iii. Max3=The dZ/dt sample corresponding to Max1 or Max2.

Note that the value of Max3 is determined according to the following logical relationships:

IF dZ/dt(2·Max1)<0.3 dZ/dt(2·Max2), THEN Max3= 2·Max2. (Eqn. 9)

IF dZ/dt(2·Max 1)>0.3 dZ/dt(2·Max2), THEN Max3= 2·Max1. (Eqn. 10)

The following exemplary output parameters are designated as part of the C point detection analysis:

C_point=the sample associated with the maximum dZ/dt (k) value within the range {Max3−2, Max3+2}.

$dZ/dt_{max}$=dZ/dt(C_point).

Figure 7:
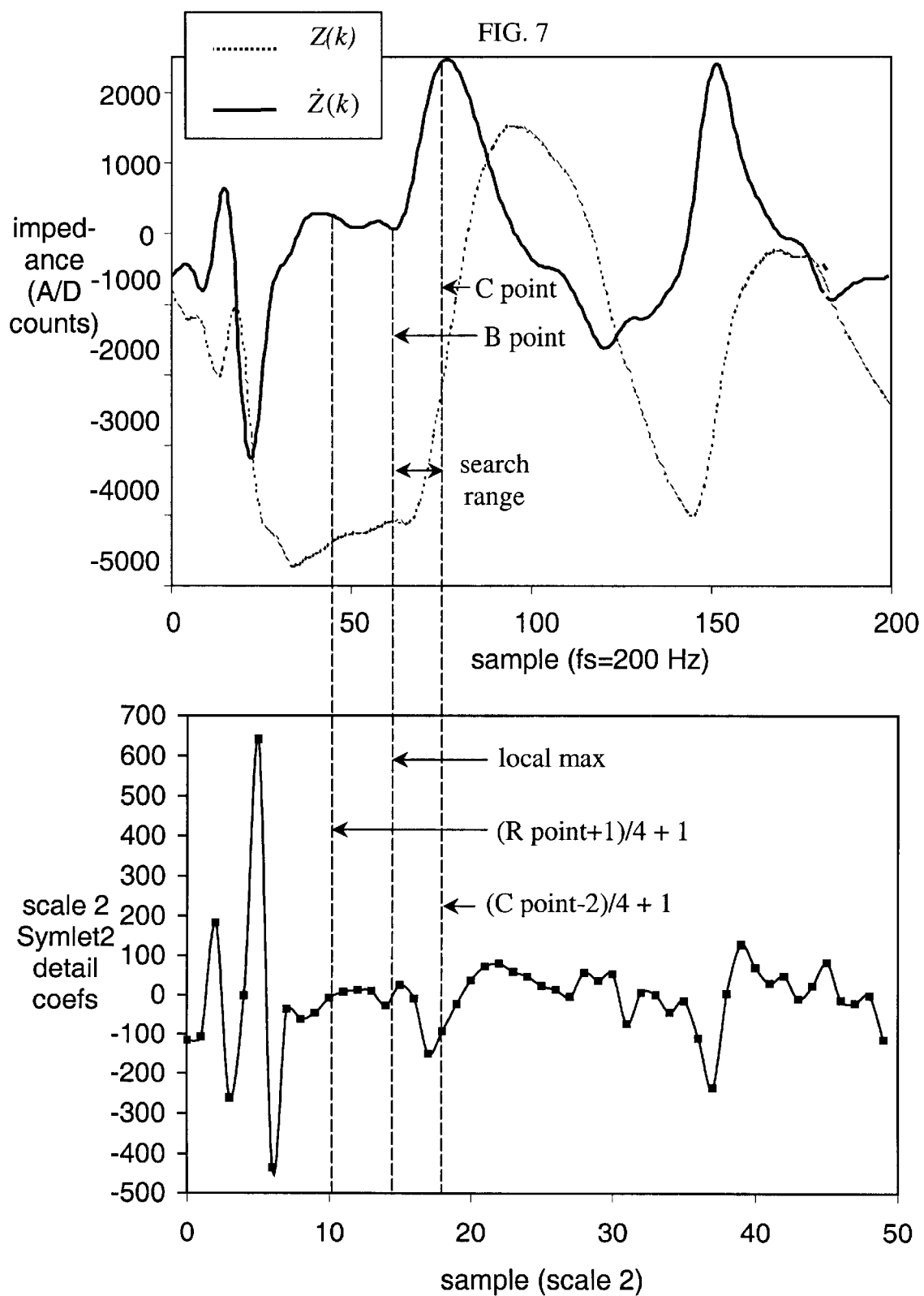
FIG. 7 is a graph illustrating exemplary B point detection using the Symlet2 wavelet filter, $s_D(k)$, according to the invention.

Per step 312 of FIG. 3, the B point is detected from scale 2 detail coefficients of ΔZ, based on an exemplary Symlet2 wavelet transform pair, illustrated in FIG. 7. The Symlet2 scaling filter, $S_A(k)$, is defined as shown in Eqn. 11:

$s_A(k)$={−0.1294, 0.2241, 0.8365, 0.4830}. (Eqn. 11)

The Symlet2 wavelet filter, $S_D(k)$, is defined as shown in Eqn. 12:

$S_D(k)$={−0.4830, 0.8365, −0.2241, −0.1294}. (Eqn. 12)

To calculate scale 2 detail coefficients, scale 1 approximation coefficients are first calculated using the scaling filter. Next, scale 2 detail coefficients are calculated from scale 1 approximation coefficients using the wavelet filter. In the illustrated embodiment, the B point is detected within the following sample range:

k={R_point, (C_point−1)}

Based on ECG detection, sample k=0 is set equal to the R point (discussed below).

The following exemplary input parameters are used in B point detection:

i. DeltaZ(k)=The time-varying portion of the impedance signal.

ii. C_point=The sample associated with $dZ/dt_{max}$.

iii. R_point=The sample associated with the maximum deflection in the QRS complex.

iv. Scale2_length=The number of scale 2 coefficients.

Similarly, the following exemplary internal parameter is used in B point detection:

i. Maxsample=The sample associated with the most recent peak scale 2 detail coefficient within the range k={[(R_Point+1)/4]+1, [(C_point −2)/4+1]}.

A "peak" is defined in the present embodiment as the sample associated with a local maximum, in which the function values immediately before and after the value at this sample are smaller, although it will be recognized that other definitions may be applied. Based on this definition, the search for the most recent local maximum is conducted from the right to left samples to obtain Maxsample, unless the following relationship applies:

IF Scale2length<5, THEN Maxsample=(R_point+1)/4.   (Eqn. 13)

The default value of Maxsample=(R_point+1)/4.

The following output parameter is used in the B point detection algorithm according to the present embodiment:

i. B_point=The global minimum DeltaZ(k) value within the range k={4·Maxsample,C_point−2}.

Figure 8:
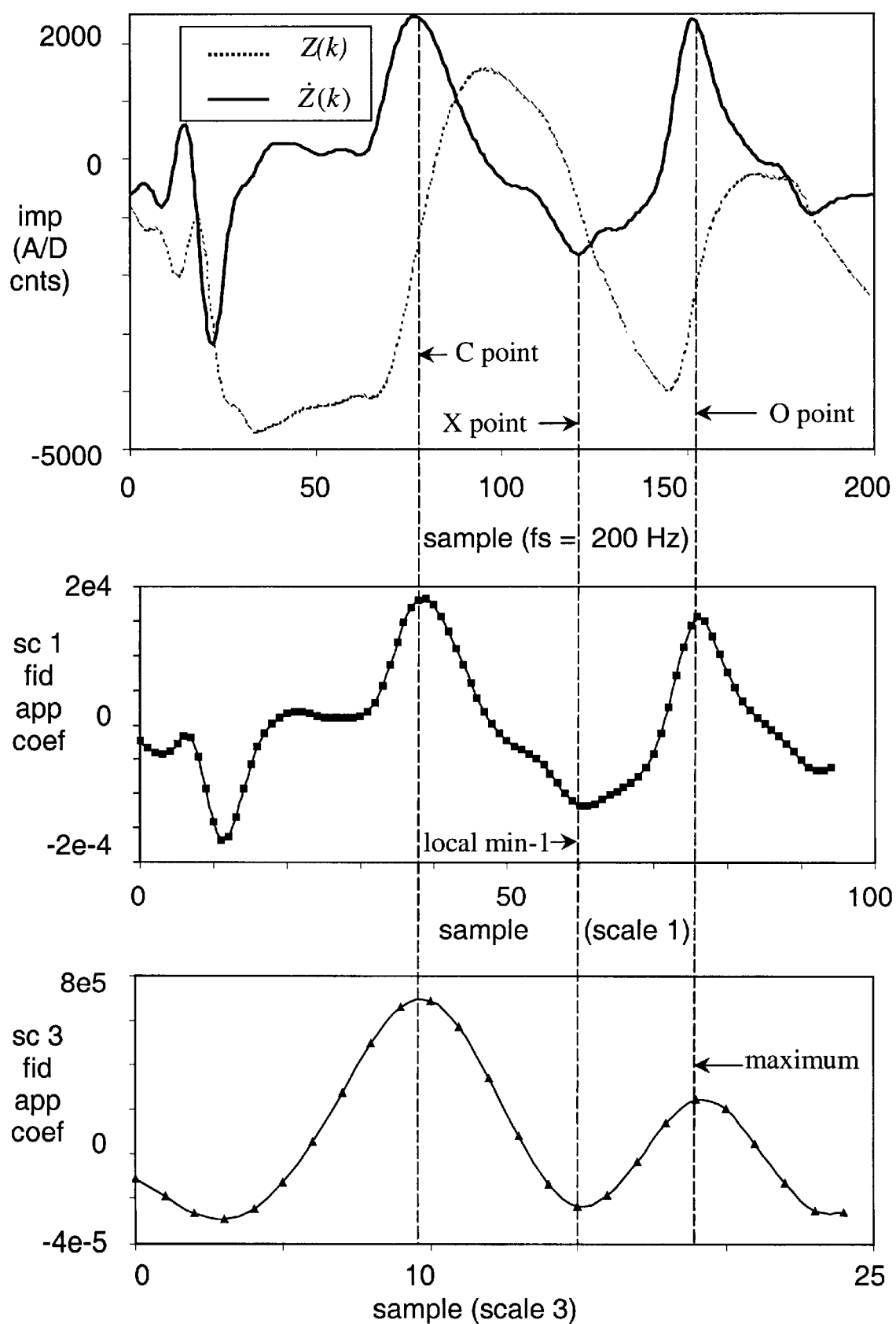
FIG. 8 is a graph illustrating exemplary X point detection using a new fiducial filter, $f_A(k)$, according to the invention.

Per step 314 of FIG. 3, the X point is detected in the present embodiment from scale 1 approximation coefficients of dZ/dt, based on a sampled version of a new continuous wavelet transform function, as shown in FIG. 8. The continuous wavelet transform function is defined in Eqn. 14:

$$x(t)=0.125t[u(t)-u(t-16)]-0.25(t-8)[u(t-8)-u(t-16)],$$   (Eqn. 14)

where u(t)=the unit step function. The corresponding fiducial filter, $f_A(k)$, is defined per Eqn. 15:

$$f_A(k)=\{0, 0.125, 0.25, 0.375, 0.5, 0.625, 0.75, 0.875, 1, 0.875, 0.75, 0.625, 0.5, 0.375, 0.25, 0.125,\}.$$   (Eqn. 15)

The X point is detected within the sample range k={(C_point+0.5 Threshold_in), (second Q point−4)}. The following exemplary input parameters are specified:

i. dZ/dt(k)=The first derivative of the impedance signal.

ii. Iteration, i The count of how often this subroutine has been called on a per beat basis.

iii. Threshold_in(i) Threshold for beginning of sample range. The initial default value=30. Threshold_in(i)= Threshold_out(i).

iv. C_point=The sample associated with the maximum dZ/dt(k) value.

Similarly, the following internal parameter is specified for X_point detection:

i. Minsample=The sample associated with the first valley scale 1 approximation coefficient within the range k={(C_point+0.5·Threshold_in(i)/2, (second Q point−1)/2}, subtracted by 1 sample.

The first valley is defined as the first increasing sample associated with a local minimum, in which the function values immediately before and after the value at this sample are greater. If a valley is not found, then Minsample=0.

The following output parameters are utilized in the X point detection:

i. X_point=The global minimum dZ/dt(k) value within the range k={2· i. X_point=The global minimum dZ/dt(k) value within the range k={2·Minsample−2, 2·Minsample+2} iii. X_point_found=Flag indicating whether X point is found. Set low if a valley is not found in the scale 1 approximation coefficient. Otherwise, set high.

iv. Threshold_out(i)=Threshold_out(i) is calculated using the following logical relationships:

a. IF i=0, THEN Threshold_out(i)=(X_point−C_point).

b. IF i≉0 AND (X_point−C_point)<1.3 Threshold in(i), THEN Threshold_out(i)=(X_point−C_point).

c. IF i≉0 AND (X_point−C_point)>1.3. Threshold_in(i), THEN Threshold_out(i)=Threshold in(i).

Per step 316 of FIG. 3, the O point is detected in the present embodiment from scale 3 approximation coefficients of dZ/dt, based on the fiducial filter, as shown in FIG. 8. The fiducial filter, $f_A(k)$, is defined as in Eqn. 15 and the O point is detected within the sample range k={X_point, (second Q point−1)}.

The following exemplary input parameters are utilized in the O point detection:

i. dZ/dt(k)=The first derivative of the impedance signal.

ii. X_point=The sample associated with the "significant" local minimum in dZ/dt(k).

The following internal parameter is utilized in the X point detection:

i. Peak=The sample associated with the peak scale 3 approximation coefficient within the range k={(X_point/8), (second Q point−1)/8}.

A peak is defined as the first increasing sample associated with a local maximum, in which the function values immediately before and after the value at this sample are less.

The following output parameter is utilized in the X point detection:

i. O_point=The O point shall be determined as the global maximum dZ/dt(k) value within the range ii. k={X_point, (8·Peak)}.

In the present embodiment, the left ventricular ejection time (LVET) is calculated per step from the B and X_points. The following exemplary input parameters are specified for the LVET calculation:

i. B_point=Sample signifying initial aortic valve opening.

ii. X_point=Sample signifying aortic valve closing.

iii. Iteration, i=Count of how often this subroutine has been called on a per beat basis.

iv. sampling_interval=time elapsed between consecutive samples

Similarly, the following output parameters are specified:

LVET(i)=The difference between the inputs, multiplied by the derivative sampling interval:

$$LVET(i)=(X\_point-B\_point)\cdot sampling\_interval.$$   (Eqn. 16)

Rejection Criteria and Median Filtering

When using prior art empirical fiducial point detection methods, it is common to reject detected points on the basis of generalized timing thresholds. However, it is known from a variety of sources including, inter alia, actual field data obtained by the Assignee hereof, that otherwise good or acceptable waveforms may be erroneously rejected if they do not meet these generalized timing thresholds. This represents another significant disability associated with prior art empirical detection techniques.

Accordingly, the present invention overcomes this disability through utilization of rejection criteria related primarily to median filtering. Based on a user-selected beat average, calculated values of LVET and $dZ/dt_{max}$ are buffered in median filters that may shift with each successive beat. The output of each filter is the median value. By using this method, erroneously large or small LVET and $dZ/dt_{max}$ values are advantageously filtered out of the stroke volume calculation. Additionally, individual beats may also be selectively rejected if the local features in the associated wavelet transforms are not present such that the X point cannot be detected.

Specifically, the input parameters for the illustrated embodiment of the median filters are defined as follows:
  i. $dZ/dt_{max}(i)$=Most recent $dZ/dt_{max}$ estimate.
  ii. LVET(i)=Most recent LVET estimate.
  iii. Iteration, i=Count of how often this subroutine has been called on a per beat basis.
  iv. Beat_average, N Number of beats to average, as determined by the user.

The median filter output parameters are defined as follows:
  i. $dZ/dt_{max\ med}$=median of $dZ/dt_{max}$, calculated according to Eqn. 17:

$$dZ/dt_{max\ med}=MEDIAN[dZ/dt_{max}(i-N+1)...dZ/dt_{max}(i)], \quad (Eqn.\ 17)$$

ii. $LVET_{med}$=median of LVET, calculated according to Eqn. 18:

$$LVET_{med}=MEDIAN[LVET(i-N+1)...LVET(i)]. \quad (Eqn.\ 18)$$

In the present embodiment, individual beats are further rejected if features are not found for proper X point detection. The following exemplary input parameter is specified for this rejection criterion:
  i. X_point_found=Bit indicating that X point was detected (e.g., set high if X point detected).

Similarly, the following output parameter is defined:
  i. Median filtering=Median filtering on/off. If the X_point is not found, the calculated $dZ/dt_{max}(i)$ is not input to the $dZ/dt_{max}$ median filter, and a default LVET(i) is not input to the LVET median filter.

It is noted that the exemplary impedance waveform fiducial point detection algorithms described above were developed and tested largely from actual data obtained from living subjects. Specifically, the data used as the basis of development and testing comprised a training set of 48 waveforms; 10 waveforms were obtained from arrhythmic patients; 10 waveforms were obtained from canines; 10 waveforms contained noise artifact; and 10 waveforms were considered noise-free. The remaining 8 waveforms were obtained from low base impedance patients.

Validation of this detection was performed by the Assignee hereof in a manner similar to the validation of QRS complexes during arrhythmias. Thirteen (13) test waveform sets were chosen randomly from a database of 266 waveforms, not used in training. Many of these waveforms possessed significant noise artifact. Additionally, 2 waveforms that exhibited bundle branch block, which occurs when the right and left ventricles do not simultaneously depolarize, were chosen. When this occurs, two R waves are present. None of the ECGs in the training data possessed bundle branch block. Fifteen (15) beats within each waveform were annotated set for each fiducial point. The annotations were used as a reference for computing detection errors in the wavelet detection algorithm and in a previously released empirical detection algorithm. Specifically, the mean absolute value error percentages were computed for LVET and $dZ/dt_{max}$.

Figure 9:
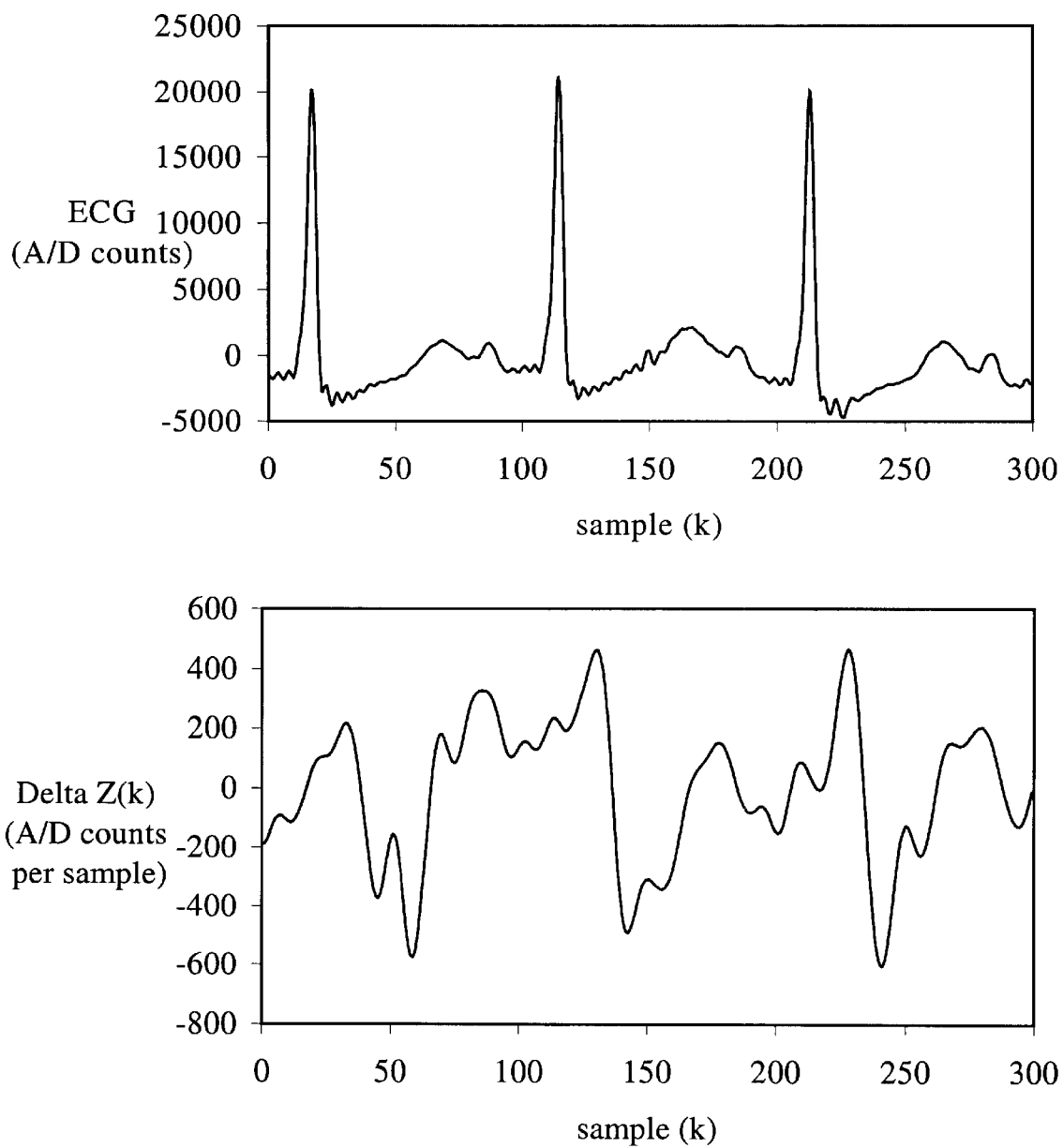
FIG. 9 is a graph illustrating a typical group of beats used in validation.

A typical group of beats selected for annotation is shown in FIG. 9. Note that these beats are much noisier than the typical examples that appear in the literature, such as FIG. 1. Based on 225 beats, LVET mean absolute error percentage decreased 48% from 19.3 to 10.0%, and $dZ/dt_{max}$ mean absolute error percentage decreased 37% from 3.0 to 1.9%, using the wavelet, rather than empirical, detection.

III. ECG Fiducial Point Detection

As with the impedance (Z) waveforms previously described, the present invention utilizes discrete wavelet transforms for QRS complex detection. QRS complexes are used to detect individual cardiac beats, and to initiate R and Q point detection. As shown in FIG. 1, the R point denotes the maximum depolarization of the QRS complex, while the Q point denotes the start of the depolarization of the QRS complex. Beat detection is also required to initiate fiducial point detection of the impedance waveform, as previously described. Accurate beat detection is also important in order to minimize the number of extraneous beats that are detected and the number of true beats that are missed, thereby increasing the accuracy of the technique.

Advantages of using wavelets in this context include, inter alia, better tolerance to noise, artifacts, and baseline drift present in the ECG signal. In one exemplary embodiment, the present invention uses the two smallest scales of the well known Haar wavelet, the wavelet with the smallest number of coefficients. In filtering, the length of the input signal needed to calculate one value of the filtered output is equivalent to the length of the filter. Therefore, the longer the filter, the longer the delay associated with the collection of the necessary input values. The number of multiplications needed to calculate one value of the filtered output is equivalent to the length of the filter. Therefore, the longer the filter, the greater number of multiplications needed. By using the shortest possible wavelet filter, the delay and number of computations required for QRS complex detection are minimized. Furthermore, a relative, rather than absolute, threshold is used for QRS detection. This approach ensures that a QRS complex will be detected regardless of its amplitude.

It will be recognized, however, that other types of wavelets (such as the family of biorthogonal or Daubechies wavelets) could be substituted for or used in conjunction with the Haar wavelets of the present embodiment, and furthermore an absolute or other type of QRS detection threshold could be specified if desired.

It is also noted that in the exemplary embodiment described below, wavelet information is used for the detection of a QRS complex only. Once a QRS complex has been detected, the R and Q points are detected using the time-based ECG values. This time-based detection allows these points to be better localized in time because these points can be found with better time resolution since wavelet transforms improve frequency localization at the expense of time localization.

Figure 10:
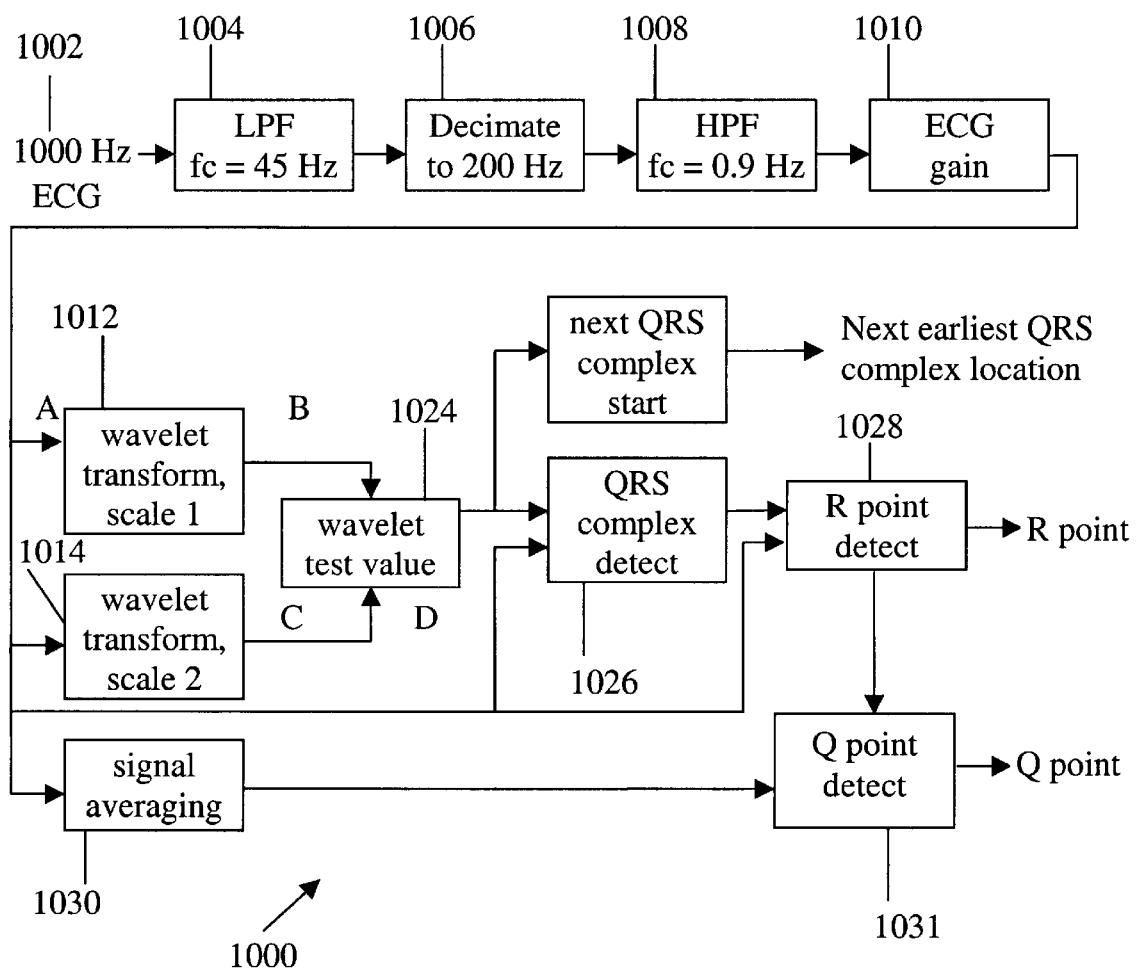
FIG. 10 is a logical flow diagram illustrating one exemplary embodiment of the method of ECG QRS complex and fiducial point detection using wavelet transforms according to the invention.

FIG. 10 illustrates one exemplary embodiment of the signal processing methodology 1000 of the invention with respect to the ECG waveform. First, the ECG waveform is sampled at a nominal rate of 1000 Hz (step 1002). The sampled ECG is then lowpass filtered with frequency cutoff of 45 Hz (step 1004) and decimated to 200 Hz (step 1006). The resulting signal is then highpass filtered with a cutoff of 0.9 Hz (step 1008), and the amplitude of the signal is altered using an auto-gain scheme (step 1010). The auto-gain converts the 21 bit value to a 16 bit value and then amplifies the signal as much as possible without saturating the 16 bits.

Next, the scale 1 and scale 2 coefficients for the resulting ECG signal are calculated (steps 1012, 1014). An intermediate test value is calculated therefrom (step 1024) by taking the square root of the absolute value of the product of the scale 1 and scale 2 coefficients of the ECG. The maximum value over the previous "i" (e.g., 48) samples, based on a 5 msec sampling interval (200 Hz sampling rate), is found in order to calculate the wavelet test value used for QRS detection. The scale 1 and scale 2 coefficients are chosen in the illustrated embodiment because these scales provide information about the high frequency content of a signal, generally associated with the QRS complex. Two scales are used in order to account for differences in frequency content across patients and pathologies. Furthermore, taking the maximum value over "i" (e.g., 48) samples helps to ignore spurious high frequency noise in the signal as well as noise from pacing spikes and high amplitude T waves, which can have overlapping frequency content.

It is noted that in contrast to the prior art, the wavelet transform is used in the present invention instead of a short-time Fourier transform (or spectrogram) because the wavelet transform provides, inter alia, better detection of non-stationary signals (signals with time-varying frequency components). This results in markedly improved time localization, and therefore better detection accuracy, of the QRS complex while decreasing the necessary computation.

As part of the QRS complex detection (step 1026), an ECG threshold is defined by multiplying 0.10 and the maximum absolute value of the previous "j" ECG samples (here, the value of "j" is set at 300, although it will be appreciated that other values may be substituted). As described in greater detail below, this ECG threshold is used, together with a wavelet test value, to detect the onset of a QRS complex. The use of a relative, rather than an absolute, threshold allows the algorithm to adjust for ECG amplitudes, which may be affected by factors such as electrode placement. This relative threshold further aids in the detection of low amplitude beats, and helps to ignore high amplitude noise in the ECG.

Once a QRS complex has been detected, the time at which it occurred is localized with better precision as part of step 1026. The result is a sample that occurs somewhere along the QRS complex. This localization is necessary because of the multiple (e.g., 48) samples over which the wavelet test value is calculated. This process helps reject artifacts, but also causes the QRS complex to be localized, at best, to an "i" sample (e.g., 48-sample) interval.

Next, the R point is localized per step 1028. The sample with the maximum absolute value of the ECG within a window located around the QRS complex is the location of the R point. R point detection per step 1028 is described in greater detail below.

The Q point is next located within a window just prior to the R point (step 1031). The ECG is optionally signal-averaged within this window (step 1030) to decrease the impact of the high frequency noise in the Q point detection. This signal averaging may be significant in certain applications, because the Q point is located along the baseline of the QRS, where the signal-to-noise ratio is lower than during the rest of the ECG. Starting from the R point and looking backward, the peak of the Q wave is found. Then, starting from the peak of the Q wave and looking backward, the beginning of depolarization of the QRS complex (i.e. Q point) is found. The Q point is further refined by searching within a window around the beginning of depolarization for the sample with the minimal deflection from the baseline. The sample at which the search for next subsequent QRS complex is disposed, specifically "m" (e.g., 48) samples past the offset of the current QRS complex, is calculated using the wavelet test value. This approach advantageously decreases unnecessary computation and helps reject undesirable artifact.

Detection of the QRS complex, R point, and Q point is accomplished using the Haar wavelet transform pair, which is composed of the Haar scaling filter, $h_A(k)$, and Haar wavelet filter, $h_D(k)$:

$$h_A(k)=[0.70710678118655\ 0.70710678118655], \quad \text{Eqn.(19)}$$

$$h_D(k)=[-0.70710678118655\ 0.70710678118655]. \quad \text{Eqn.(20)}$$

Figure 5:
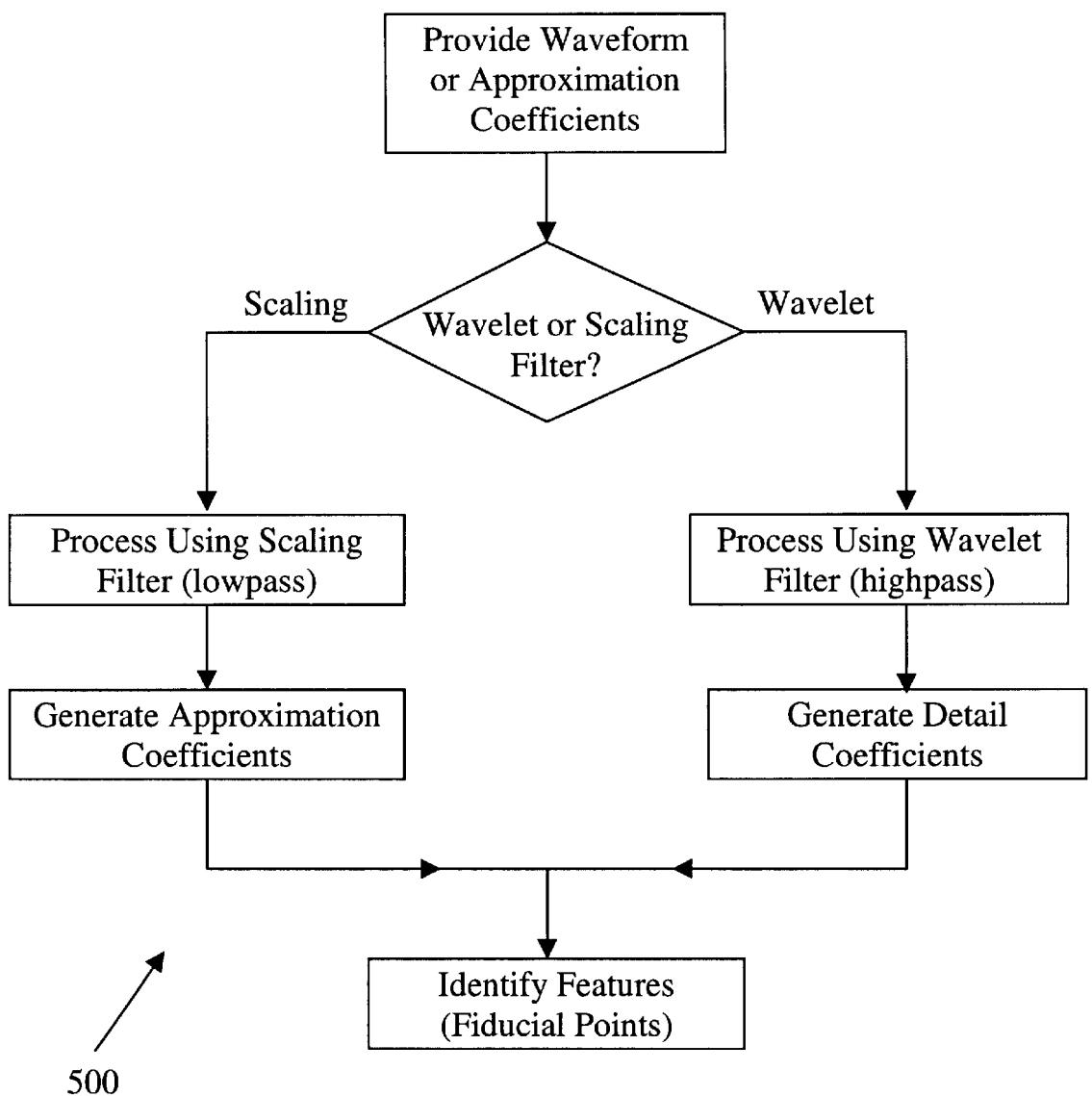
FIG. 5 is a logical block diagram illustrating the process of waveform filtering using scaling (lowpass) or wavelet filters (highpass) according to the invention.

Wavelet transforms, consisting of approximation or detail coefficients, are calculated, as per FIG. 5.

Detection of the QRS complex (step 1026 of FIG. 10) is now described in detail. In the present embodiment, the sole input parameter for QRS complex detection comprises the 200 Hz ECG signal, x(k). Seven internal parameters are defined as follows:

(i) Wavelet transform-scale 1, $WT_{s1}(k)$ (ii) Wavelet transform-scale 2, $WT_{s2}(k)$ (iii) Repeated version of $WT_{s1}(k)$, $WT_{s1}'(k)$ (iv) Repeated version of $WT_{s2}(k)$ $WT_{s2}'(k)$ (v) Wavelet test value, $W_T(k)$ (vi) QRS threshold, threshold(k)

(vii) QRS threshold crossing, crossing(k).

Each of these seven parameters are described in greater detail below.

(i) Wavelet Transform-Scale 1, $WT_{s1}(k)$

The exemplary Haar wavelet transform is used to find the detail coefficients at scale 1 of the ECG signal. This output is denoted as $WT_{s1}(k)$, and is illustrated in FIG. 11b.

(ii) Wavelet Transform-Scale 2, $WT_{s2}(k)$

The Haar wavelet transform is used to find the detail coefficients at scale 2 of the ECG signal. This output is denoted as $Y_{s2}(k)$, and is illustrated in FIG. 11c.

(iii) Repeated Version of $WT_{s1}(k)$, $WT_{s1}'(k)$

Each value of $WT_{s1}(k)$ is repeated once as illustrated in FIG. 11d. Thus, there is one value of $WT_{s1}'(k)$ for each sample of the 200 Hz ECG.

(iv) Repeated Version of $WT_{s2}(k)$, $WT_{s2}'(k)$

Each value of $WT_{s2}(k)$ is repeated three times as illustrated in FIG. 11e. Thus, there is one value of $WT_{s2}'(k)$ for each sample of the 200 Hz ECG.

(v) Wavelet test value, $W_T(k)$—The wavelet test value, $W_T$, is calculated according to Eqns. 21 and 22 below:

$$w(k)=\sqrt{|y'_{s1(k)}y'_{s2(k)}|} \quad \text{(Eqn. 21)}$$

$$W_T(k)=\max w(i),\ i\in[k-HR_{max},k],\ \text{where}\ HR_{max}=48. \quad \text{(Eqn. 22)}$$

(vi) QRS threshold, threshold(k)—The QRS threshold is calculated according to Eqn. 23:

$$\text{threshold}(k)=0.10\max |x(k-300:k)| \quad \text{(Eqn. 23)}$$

(vii) QRS threshold crossing, crossing(k)—The wavelet test value, $w_T$, calculated in via Eqn. 22 above, is used to detect the presence of a QRS complex, using Eqns. 24 and 25 below:

$$w_T(k)>\text{threshold and}\ w_T(k)\leq 1.05\cdot w_T(k+2) \quad \text{(Eqn. 24)}$$

$$w_T(k)>w_T(k+1)\ \text{and}\ w_T(k)>w_T(k+30) \quad \text{(Eqn. 25)}$$

Note that if Eqn. 24 is satisfied, then crossing(k)=1. If Eqn. 24 is not satisfied, but Eqn. 25 is satisfied, then crossing (k)=0. If both Eqns. 24 are not satisfied, then crossing(k)= crossing(k−1).

The sole output parameter defined in the present embodiment of the QRS detection methodology is QRS complex location, $k_{QRS}(m)$, where:

$m \in [0, \ldots, M]$, M+1=number of QRS complexes

The start of the QRS window is defined as the first sample in which the QRS threshold has been crossed, i.e., crossing (k)=1 and crossing (k−1)=0. The end of the QRS window is defined as the first sample after the start of the QRS window in which the QRS threshold has not been crossed, i.e., crossing (k)=0 and crossing (k−1)=1.

The location of the QRS complex within the QRS window is first analyzed. Starting from the end of the window and decrementing by one sample until the start of the window has been reached, the first sample satisfying the condition $w_T(k) < w_T(k+1)$ (if found) is identified. The sample k+1 shall be designated as the location of the QRS complex, i.e., qrs(m)=k+1. The default of location of the QRS complex is the start of the window.

FIGS. 11a–11g illustrate the foregoing processes graphically.

The detection of the R point according to step 1028 of FIG. 10 is now described. As with the QRS complex detection methodology described above, R point detection according to the present embodiment utilizes the nominal 200 Hz ECG signal, x(k) as the sole input parameter. The sole output parameter comprises the R point location, $k_R(m)$, where:

$m \in [0, \ldots, M]$, M+1=number of QRS complexes

The location of the R wave is defined as that sample in which the absolute value of the ECG signal is maximal within a window that starts at "a" samples before the QRS complex location and ends at "b" samples after the QRS complex location. In the exemplary embodiment, a=20 and b=30, although it will be recognized that other values may be used with success.

Detection of the Q point (step 1031 of FIG. 10) is now described. As with the R point and QRS complex detection methodologies described above, Q point detection according to the present embodiment utilizes the nominal 200 Hz ECG signal, x(k) as the sole input parameter. The sole internal parameter defined comprises the signal-averaged version (step 1030 of FIG. 10) of the original 200 Hz ECG signal, $X_{avg}(k)$, where:

$$X_{avg}(K) = \overline{x(i)}, i \in [k-5, k+5]$$

The sole output parameter is Q point location, $k_Q(m)$, where:

$m \in [0, \ldots, M]$, M+1=number of QRS complexes

Starting at "c" samples before the location of the R point and ending at "d" samples before the location of the R point, the first sample k in which $x_{avg}(k) < x_{avg}(k-1)$ or $|x_{avg}(k)| < 100$, where $x_{avg}$ is the signal-averaged ECG, is found. In the illustrated embodiment, c=6 and d=80, although other values may be substituted. Then, starting from "e" samples before k and ending at "f" samples before the location of the R point, the first sample k in which either Eqn. 26 or 27 below is valid is found:

$$x_{avg}(k_R) > 0.0 \text{ and } |x_{avg}(k)| \geq 0.95 \cdot x_{avg}(k-2)| \quad \text{(Eqn. 26)}$$

$$x_{avg}(k_R) \leq 0.0 \text{ and } |x_{avg}(k)| \leq 0.95 \cdot x_{avg}(k-2) \quad \text{(Eqn. 27)}$$

where $k_R$ is the location of the R point in the present embodiment, e=2 and f=80, although other values may be chosen. The default k shall be 80 samples before the location of the R point.

Calculate the baseline value according to Eqn. 28:

$$baseline(m) = \frac{1}{7} \sum_{i=k-10}^{k-4} x_{avg}(i) \quad \text{(Eqn. 28)}$$

Starting at 3 samples before k and ending at 3 samples after k, find the first sample whose signal-averaged ECG value is nearest the baseline value, i.e., the first sample j in which Eqn. 29 holds:

$$|x_{avg}(j) - baseline(m)| \geq |x_{avg}(i) - baseline(m)|, \forall i \in [k-3, k+3] \quad \text{(Eqn. 29)}$$

This sample, j, is the location of the Q point, $k_Q(m)$.

Detection of the next subsequent QRS complex (step 1034 of FIG. 10) according to the present embodiment utilizes the wavelet test value, $w_T(k)$, and the QRS threshold, threshold(k), as input parameters. The output parameters comprise the sample number to begin looking for next QRS complex, $k_{start}(m+1)$, where:

$m \in [0, \ldots, M]$, M+1=number of QRS complexes

Starting at the beginning of the QRS window and incrementing by one, the waveform is analyzed to find the first sample k for which $w_T(k) < 3 \cdot threshold(k)$. $k_{start}(m)$ occurs "m" (e.g., 48) samples past this first sample. The default value is defined as the second sample, i.e., $k_{start}(0) = 1$.

Rejection criteria for the QRS analyses described above are defined in terms of the following input parameters:

(i) 200 Hz ECG signal, x(k)

(ii) Q point location, $k_Q$ m), where:
$m \in [1, \ldots, M]$, M+1=number of QRS complexes (iii) R point location, $k_R$m), where:
$m \in [1, \ldots, M]$, M+1=number of QRS complexes The following exemplary internal parameters are defined:

(i) absolute amplitude of the 200 Hz ECG signal at the R point location, $x_R(m)$, where:
$m \in [0, \ldots, M]$, M+1 number of QRS complexes
$x_R(m) = |x(k_R(m))|$ (ii) current R to R interval, $I_{R-R}(m)$, where:
$I_{R-R}(m) = k_R(m) - k_R(m-1)$ (iii) mean R to R interval of the prior ten beats, $\overline{I_{R-R}}(m)$, where:
$\overline{I_{R-R}}(m) = \overline{k_{R(i)} - k_{R(i-1)}}, i \in [m-11, m-1]$ (iv) current R to Q interval, $I_{R-Q}(m)$, where:
$I_{R-Q}(m) = k_R(m) - k_Q(m)$ (v) mean R to Q interval of the last ten beats, $\overline{I_{R-Q}}(m)$, where:
$\overline{I_{R-Q}}(m) = \overline{k_R(i) - k_Q(i)}, i \in [m-11, m-1]$ (vi) Maximum R-R interval rejection criterion, $R_1(m)$, where:
If $I_{R-R}(m) > 3 \cdot \overline{I_{R-R}}(m)$, $R_1(m) = 1$.
Otherwise, $R_1(m) = 0$.

(vii) Minimum R-R interval rejection criterion, $R_2(m)$, where:
If $I_{R-R}(M) < 0.3 \cdot I_{R-R}(m)$, $R_2(M) = 1$.
Otherwise, $R_2(M) = 0$.

(viii) R wave amplitude rejection criterion, $R_3(m)$, where:
If $x_R(M) < 0.15 \cdot x_R(m-1)$ and the patient is paced, $R_3(m) = 1$.
Otherwise, $R_1(m) = 0$.

(ix) Maximum R-Q interval rejection criterion, $R_4(m)$, where:
Otherwise, $R_4(m) = 0$.

(x) Minimum R-Q interval rejection criterion, $R_5(m)$
If $I_{R-Q}(m) < 0.3 \cdot \overline{I_{R-Q}}(m)$, $R_5(m) = 1$.

Otherwise, $R_5(m)=0$.

(xi) Q point not found rejection criterion, $R_6(m)$, where:
A beat is rejected if the Q point is not found (defaults to the edge of the Q window), i.e., $I_{R-Q}(m)=80$. If this condition occurs, $R_6(m)=1$ Otherwise, $R_6(m)=0$.

The following output parameters are defined for the rejection criteria:

(i) reject b eat, reject(m), where:
reject(m)=$R_1(m)$ $\lor R_2(m)$ $\lor R_3(m)$ $\lor R_4(m)$ $\lor R_5(m)$ $\lor R_6(m)$ Beat m is rejected if reject(m)=1. Beat m is accepted if reject(m)=0.

It is further noted that while the rejection criteria documented here are based on the acceptance of "good" beats in the training waveforms, and not, conversely, on the rejection of "bad" beats", alternate rejection criteria based on "bad" beats, or even a combination or aggregation of either type of criteria, may be employed consistent with the invention.

As with the impedance waveform fiducial point detection algorithm described above, the ECG fiducial point detection algorithm was developed and tested based on actual data obtained from living subjects. The data comprised 23 previously collected patient files (146 waveforms total). The ECG fiducial point detection algorithm was validated using the same 15 test files and methodology that were used to validate the impedance fiducial point detection algorithm. Based on 225 beats, Q point mean absolute error percentage decreased 88% from 79.3 to 9.4%, using the wavelet, rather than empirical, detection.

IV. Apparatus for Hemodynamic Assessment

Figure 12:
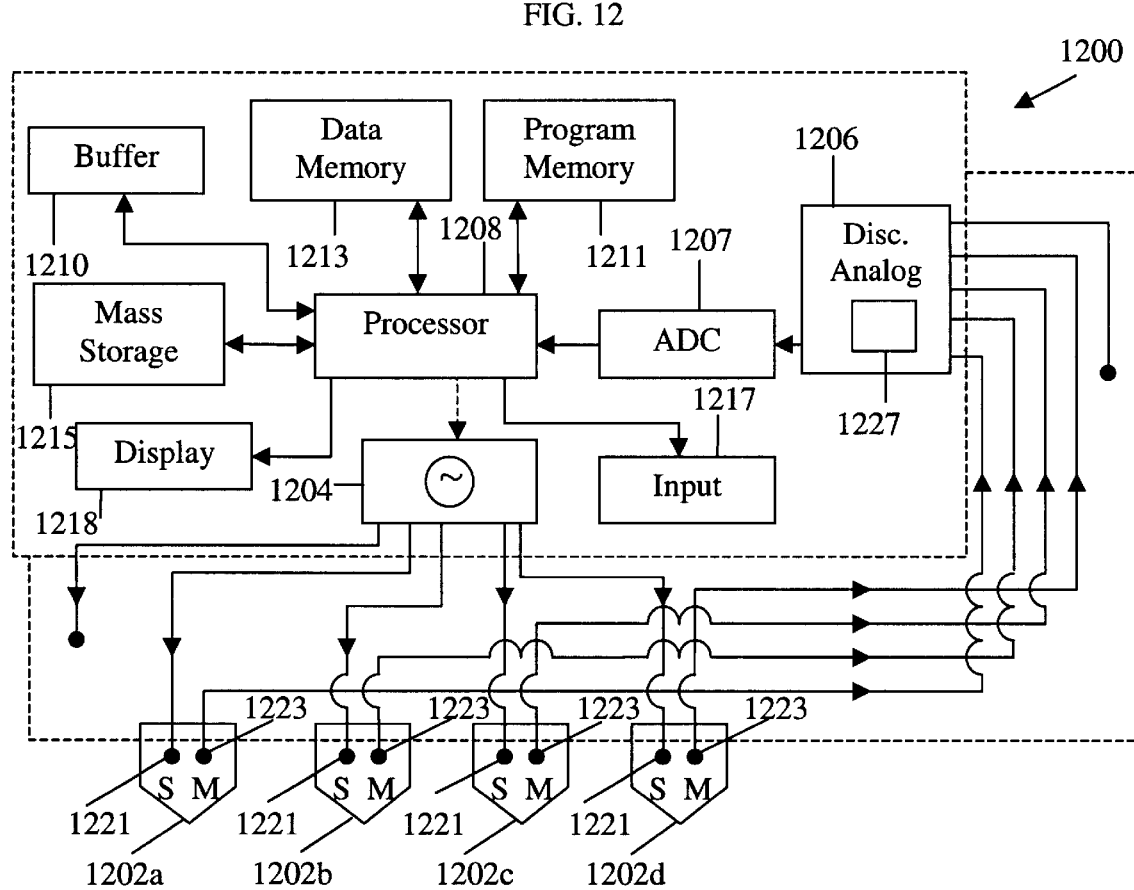
FIG. 12 is a block diagram of one exemplary embodiment of the apparatus for hemodynamic assessment according to the invention.

Referring now to FIG. 12, an apparatus for measuring hemodynamic properties associated with the cardiovascular system of a living subject is described. In the illustrated embodiment, the apparatus is adapted for the measurement of the cardiac output of a human being, although it will be recognized that other hemodynamic parameters and types of living organism may be evaluated in conjunction with the invention in its broadest sense.

The apparatus 1200 of FIG. 12 fundamentally comprises a plurality of electrically conductive electrodes 1202 (with individual terminals 1221, 1223) for supplying a current and measuring voltage (and impedance) from the subject non-invasively; a current source 1204 coupled to at least a portion of the electrodes 1202 for providing the alternating (AC) electrical current supplied to the subject; discrete analog circuitry 1206 for preconditioning the analog impedance and ECG waveforms derived from the electrodes 1202; an analog-to-digital converter (ADC) 1207 for converting the conditioned analog signals to a binary digital format; a digital processor 1208 operatively connected to the ADC 1207 for analyzing the digital representations of the conditioned ECG and impedance waveforms; a buffer memory 1210 for storing conditioned data prior to fiducial point detection; program and data memories 1211, 1213, for storing program instructions and data, respectively; a mass storage device 1215, an input device 1217 for receiving operation command and data from the apparatus user, and a display device 1218 for displaying information such as data and waveforms, as well as applications program interface, to the user.

The electrodes 1202 of the embodiment of FIG. 12 comprise so-called "spot" electrodes of the type well known in the medical arts, although it will be recognized that other types of electrodes, including band electrodes may be substituted. As used herein, the term "spot" electrode includes both single- and multi-terminal electrodes adapted for use in a localized area of the subject's physiology. Exemplary configurations of the multi-terminal spot electrode especially useful with the invention herein are described in co-pending U.S. utility and design patent applications, Ser. Nos. 09/613,183 and 29/128,623 respectively, filed Jul. 10, 2000 and Aug. 28, 2000, respectively, both assigned to the Assignee hereof, both incorporated by reference herein in their entirety.

In operation, the apparatus 1200 generates an effectively constant current (via the current source 1204) which is applied to certain ones of the terminal(s) 1221 of the electrodes 1202. The applied current derived from the current source 1204 is a 70 kHz sine wave of approximately 2.5 mA maximum RMS. The measured voltage associated with the aforementioned sine wave is on the order of 75 mV maximum RMS. These values are chosen to advantageously minimize electric shock hazard, although it will be appreciated that other frequencies, currents, or voltages may be substituted. The construction and operation of AC current sources is well known in the electronic arts, and accordingly is not described further herein.

The preprocessor 1206 and associated signal processing apparatus is in electrical communication with other electrodes 1202, from which potentials (voltages) are measured. In the selected frequency range of the AC signal (e.g., 70 kHz), the typical impedance associated with a human subject's skin is 2 to 10 times the value of the underlying thoracic impedance $Z_T(t)$. To aid in eliminating the contribution from skin and tissue impedance, the apparatus of the present invention uses at least two, and typically four electrode arrays 1202a–d for measurement, as shown in FIG. 12. In a simple application, one electrode array 1202a comprising a stimulation electrode terminal 1221 and a measurement electrode terminal 1223 is applied above the thorax of the subject, while a second electrode array 1202b (similarly having a stimulation electrode terminal and measurement electrode terminal) is applied below the thorax. The AC current from the current source is supplied to the stimulation electrode terminals 1221. Current flows from each stimulation electrode terminal 1221 through each constant skin impedance, $Z_{sk1}$ or $Z_{sk4}$, each constant body tissue impedance, $Z_{b1}$ or $z_{b1}$, and each constant skin impedance, $Z_{sk2}$ or $Z_{sk3}$, to each measurement electrode terminal 1223. The voltages at the measurement electrode terminals 1223 are measured and input to a differential amplifier circuit 1227 within the preprocessor 1206 to obtain the differential voltage, $V_T(t)$. The desired thoracic impedance, $Z_T(t)$, is then obtained using the relationship of Eqn. 30.

$$Z_T(t) = \frac{V_T(t)}{I_T(t)} \qquad \text{(Eqn. 30)}$$

As shown in FIG. 12, two sets of electrode arrays 1202a–d may advantageously be used to monitor the impedance associated with the left and right portion of the thorax in the present invention. When eight electrode terminals (four arrays 1202a–d each with two terminals 1221, 1223) are used in this manner, the four measurement arrays are also used to obtain an electrocardiogram (ECG). As previously discussed, the Q wave of the ECG QRS interval is used to, inter alia, determine the subject's heart rate, identify the QRS complex and Q and R points, and as an input to the fiducial point detection algorithm for the impedance waveform.

It is noted that the apparatus 1200 described herein may be constructed in a variety of different physical configurations, using a variety of different components, and measuring a variety of different hemodynamic parameters.

For example, some or even all of the foregoing components may be physically integrated (such as in an application specific integrated circuit incorporating a DSP core, memory, "front" end analog processing, and ADC in a single piece of silicon), and/or the functionality associated with multiple components performed by a single multi-function component (e.g., a processor adapted to perform calculations associated with the wavelet transform methods disclosed herein, as well as host functions such as video display, bus arbitration, etc.). One exemplary configuration comprises a PC-based device of the type well known in the art, having a host microprocessor as well as the aforementioned preprocessing and signal processing functionality in the form of a separate DSP in data communication therewith. In yet another embodiment, the apparatus comprises a mobile personal computing device (such as a personal digital assistant, or PDA), which is adapted to receive input data from the electrodes 1202 and analyze the data to produce a corrected measurement of cardiac output. It will also be recognized that other portable devices, such as laptop computers, calculators, and personal organizers, may conceivably be configured to run the computer program(s) of the present invention. Such portable devices are readily adapted to the methods of the present invention, since as a result of the invention's advantageous use of comparatively simple wavelet transforms, the processing and storage capability needed to implement the algorithm is decreased. Furthermore, a variety of different methods of transmitting the input sensor (i.e., electrode) data to these devices may be used, including networked computers, or even wireless data links.

Furthermore, cardiac output, LVET, SV, or other measurements generated by the foregoing apparatus 1200 may also optionally be stored in the storage device 1215 for later retrieval, or output to an external device such as a printer, data storage unit, other peripheral component via a serial or parallel port if desired. Furthermore, the apparatus 1200 may be networked to another computing device or database (not shown) whereby the data generated by the apparatus may be remotely analyzed or stored. Transmission of output data to such remote devices may be accomplished using a variety of well understood methods, such as by local area network (LAN), intranet, Internet, fiber-optic systems, or radio frequency (wireless) devices.

It will be further recognized that while the apparatus 1200 of the invention is described herein as a substantially discrete or "stand-alone" system, the invention may be adapted to act as a plug in card, module, or other complementary device (including any supporting software) for an existing ECG or patient monitoring system that utilizes electrodes. Hence, the invention can advantageously be "retrofitted" to such prior art systems, thereby extending the utility of the pre-existing system, and potentially obviating the purchase of entirely new equipment.

V. Computer Program

A computer program for implementing the aforementioned methods of impedance and ECG waveform analysis is now described. In one exemplary embodiment, the computer program comprises an object ("machine") code representation of an assembly source code listing implementing the discrete wavelet transform waveform analysis methodologies previously described herein, either individually or in combination thereof. While assembly language is used for the present embodiment, it will be appreciated that other programming languages may be used, including for example VisualBasic™, Fortran, C, and C++. The object code representation of the source code listing is compiled and disposed on a media storage device of the type well known in the computer arts. Such media storage devices can include, without limitation, optical discs, CD ROMs, magnetic floppy disks or "hard" drives, tape drives, or even magnetic bubble memory. The computer program further comprises a graphical user interface (GUI) of the type well known in the programming arts, which is operatively coupled to the display and input device of the host computer or apparatus 1200 on which the program is run.

In terms of general structure, the program is in one embodiment comprised of a series of subroutines or algorithms for implementing the methodologies described herein based on measured parametric data (e.g., the "input parameters" previously defined) which are provided to the host computer. In a second embodiment, the computer program comprises an assembly language/micro-coded instruction set disposed within the embedded storage device, i.e. program memory, of a digital signal processor (DSP) or microprocessor associated with the foregoing hemodynamic measurement apparatus of FIG. 13.

VI. Method of Providing Treatment

Referring now to FIG. 13, a method of providing treatment to a subject using the aforementioned methods of wavelet transform fiducial point detection is described. While the following discussion is cast in terms of the aforementioned methods and algorithms adapted for determining cardiac output, it will be recognized that the method or providing treatment described herein is more broadly applicable to treatment based on the assessment of any hemodynamic property or parameter based on discrete wavelet transform analysis.

As shown in FIG. 13, the method of providing treatment 1300 generally comprises first disposing a plurality of impedance cardiography electrodes with respect to the thoracic cavity of the subject per step 1302. As previously discussed, the electrodes 1202 are the multi-terminal type described above with respect to FIG. 13 (or other suitable configuration), and are disposed above and below the thorax of the subject such that at least one stimulation terminal and one excitation terminal are above and below the thorax. Next, the impedance waveform (and ECG) data of the subject are measured non-invasively via the electrodes 1202 per step 1304; specifically by applying a constant AC waveform to the stimulation terminal(s), and measuring the resultant voltage at the measurement terminal(s). In step 1306, the stroke volume of the subject's cardiac muscle during at least one cardiac cycle is determined using discrete wavelet transforms as previously discussed herein. Specifically, after signal conditioning and pre-processing, the B, C, O, and X fiducial points are detected within the impedance waveform, and the QRS complex(es) and associated Q and R points are detected within the ECG waveforms, using the wavelet transforms. The stroke volume is then determined from the derived values of LVET and $dZ/dt_{max}$. The cardiac output (CO) of the subject is next determined in step 1308 based on the stroke volume determined in step 1306, and the heart rate (HR) derived from the subject from the ECG waveform.

Lastly, a course of treatment is determined and provided to the subject based on the cardiac output (CO) of step 1308. Such course of treatment may include, for example, the intravenous injection of pharmacological agents, angioplasty, or other such measures aimed at increasing cardiac output or otherwise stemming further degradation of the subject's cardiac function.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of assessing cardiac output within a living subject, comprising:
   providing a plurality of electrodes disposed relative to the thoracic cavity of said subject;
   passing an electrical current through at least a portion of said thoracic cavity;
   measuring at least one impedance waveform associated with said thoracic cavity using said current and at least one of said plurality of electrodes;
   processing said at least one impedance waveform using discrete wavelet transforms to identify one or more fiducial points within said at least one impedance waveform; and
   determining cardiac output based at least in part on said one or more fiducial points.

2. The method of claim 1, wherein the act of processing said at least one impedance waveform comprises identifying a plurality of B, C, X, and O points of the $\Delta Z$ and $dZ/dt$ waveforms.

3. The method of claim 2, wherein the act of determining cardiac output comprises determining left ventricular ejection time (LVET).

4. The method of claim 3, wherein the act of determining LVET comprises determining the difference between respective ones of said plurality of X and B points.

5. The method of claim 3, further comprising:
   determining the magnitude of the largest negative derivative of the impedance change occurring during systole ($dZ/dt_{max}$) from said C point;
   determining the stroke volume from at least LVET and $dZ/dt_{max}$; and
   determining cardiac output based at least in part on said stroke volume.

6. The method of claim 2, wherein said act of identifying said plurality of B, C, X, and O points comprises detecting at least one C point using a Mallet scaling filter, $m_A(k)$.

7. The method of claim 2, wherein said act of identifying said plurality of B, C, X, and O points comprises detecting at least one B point using scale 2 detail coefficients of $\Delta Z$, using a Symlet2 scaling filter, $s_A(k)$, and wavelet filter, $s_D(k)$.

8. The method of claim 7, wherein said act of identifying said plurality of B, C, X, and O points comprises detecting at least one B point using scale 2 detail coefficients of $\Delta Z$, using a Symlet2, scaling filter, $s_A(k)$, and wavelet filter, $s_D(k)$.

9. The method of claim 2, wherein said act of identifying said plurality of B, C, X, and O points comprises detecting at least one X point using scale 1 approximation coefficients of $dZ/dt$ based on a fiducial filter, $f_A(k)$.

10. A method of assessing a hemodynamic parameter within a living subject, comprising:
    disposing a plurality of electrodes relative to said subject;
    measuring at least one impedance waveform from said subject using at least one of said plurality of electrodes;
    processing said at least one impedance waveform using at least one wavelet transform to identify one or more fiducial points within said at least one impedance waveform; and
    assessing said hemodynamic parameter based at least in part on the one or more of said fiducial points.

11. The method of claim 10, wherein the act of assessing comprises assessing the stroke volume of the heart of said subject.

12. The method of claim 11, wherein the act of disposing comprises disposing at least a portion of said plurality of electrodes relative to the thoracic cavity of said living subject.

13. The method of claim 12, wherein the act of processing said at least one impedance waveform comprises identifying a plurality of B, C, X, and O points of the $\Delta Z$ and $dZ/dt$ waveforms, and the act of determining cardiac output comprises determining left ventricular ejection time (LVET) by determining the difference between respective ones of said plurality of X and C points.

14. The method of claim 13, further comprising:
    determining the magnitude of the largest negative derivative of the impedance change occurring during systole ($dZ/dt_{max}$) from the C point; and
    determining the stroke volume from at least LVET and $dZ/dt_{max}$.

15. A method of detecting events within the electrocardiogram (ECG) of a living subject, comprising:
    disposing at least one electrode relative to the thoracic cavity of said subject;
    measuring at least one ECG waveform using said at least one electrode; and
    processing said at least one ECG waveform using discrete wavelet transforms to identify one or more events within said ECG waveform.

16. The method of claim 15, wherein said events comprise fiducial points, said method further comprising:
    identifying at least one QRS complex based at least in part on said one or more fiducial points; and
    identifying beats based at least in part on said at least one QRS complex.

17. The method of claim 16, further comprising:
    detecting the R point in said at least one QRS complex; and
    detecting the onset of depolarization of said QRS complex (Q point) in said at least one complex.

18. The method of claim 17, wherein the act of detecting at least one QRS complex comprises determining the detail coefficients using a Haar wavelet transform pair.

19. The method of claim 18, wherein the act of determining the detail coefficients using a Haar wavelet transform comprises determining the scale 1 and scale 2 detail coefficients.

20. An information storage device, comprising;
    a data storage medium;
    a plurality of data stored on said medium, said plurality of data comprising a computer program adapted to run on a data processor, said computer program being configured for determining at least one value of a first hemodynamic parameter of a living subject based on first input data and second input data, said first input data being representative of an impedance waveform, said second input data being representative of a an electrocardiographic (ECG) waveform, the act of determining said at least one value of said first hemodynamic parameter comprising:

processing said at least one impedance waveform using wavelet transforms to identify at least one fiducial point therein;

processing said at least one ECG waveform using wavelet transforms to identify at least one fiducial point therein; and determining said at least one value of said first hemodynamic parameter based at least in part on said at least one fiducial points from said impedance and ECG waveforms, respectively.

21. The information storage device of claim 20, wherein said computer program is further adapted to calculate values of left ventricular ejection time (LVET) and $dZ/dt_{max}$, said value of LVET being related at least in part to said at least one fiducial point of said at least one impedance waveform.

22. The information storage device of claim 21, wherein said computer program is further adapted to estimate stroke volume based at least in part on said values of LVET and $dZ/dt_{max}$.

23. The information storage device of claim 20, wherein said data storage medium comprises a portable magnetic disk medium, and said computer program comprises an object code representation of a source code listing.

24. Apparatus for assessing at least one hemodynamic parameter associated with a living subject comprising;

a plurality of electrodes adapted to be disposed in proximity to the thoracic cavity of the subject;

a current source adapted to provide an electrical current through at least a portion of said thoracic cavity via at least a first of said plurality of electrodes, and produce an impedance waveform relating thereto on at least a second of said plurality of electrodes; and a signal processing apparatus, operatively coupled to said at least second of said plurality of electrodes, said signal processing apparatus adapted to analyze said impedance waveform using wavelet transforms to assess said at least one hemodynamic parameter.

25. The apparatus of claim 24, wherein said at least one hemodynamic parameter comprises stroke volume, and at least one of said plurality of electrodes comprises a spot electrode having a plurality of electrically conductive terminals disposed thereon.

26. The apparatus of claim 25, wherein said spot electrode comprises two terminals, and said two terminals are spaced at a predetermined distance from each other.

27. The apparatus of claim 24, wherein said signal processing apparatus is further adapted to measure at least one electrocardiographic (ECG) waveform via at least one of said plurality of electrodes, and analyze said ECG waveform using wavelet transforms.

28. The apparatus of claim 24, wherein said signal processing apparatus comprises:

signal conditioning apparatus adapted to condition at least said impedance waveform;

an analog-to-digital converter to convert at least a portion of said impedance waveform to binary digital format data; and a digital processor adapted to run at least one computer program thereon, said at least one computer program being configured to calculate at least one wavelet transform based on said binary digital format data.

29. The apparatus of claim 28, wherein said digital processor comprises a digital signal processor (DSP), and at least a portion of said computer is disposed within an embedded memory associated therewith.

30. The apparatus of claim 27, wherein said signal processing apparatus is adapted to identify at least one QRS complex using said wavelet transforms.

31. The apparatus of claim 27, wherein said signal processing apparatus is adapted to identify at least one Q point within said ECG waveform, said analysis of said impedance waveform using wavelet transforms being dependent at least in part upon said at least one Q point.

32. A signal processing apparatus adapted for analyzing waveforms obtained from a living subject, comprising:

an analog-to-digital converter to convert at least a portion of said waveforms to binary digital format data; and a digital processor adapted to run at least one computer program thereon, said at least one computer program being configured to calculate at least one wavelet transform based on said binary digital format data.

33. The apparatus of claim 32, further comprising signal conditioning apparatus adapted to condition at least a portion of said waveform prior to conversion thereof to said binary digital format.

34. The apparatus of claim 33, wherein said conditioning of said at least portion of said waveform comprises:

(i) band pass filtering; and (ii) decimation.

35. The apparatus of claim 32, wherein said at least one computer program is adapted to:

identify, using at least one wavelet transform, the B, C, O, and X points within an impedance waveform; and identify, using at least one wavelet transform, at least one QRS complex within an ECG waveform.

36. The apparatus of claim 35, wherein said C point is detected using a Mallet scaling filter, $m_A(k)$.

37. The method of claim 35, wherein said B point is detected using scale 2 detail coefficients of $\Delta Z$ based on a Symlet2 scaling filter, $s_A(k)$, and wavelet filter, $s_D(k)$.

38. The method of claim 35, wherein said X point is detected using scale 1 approximation coefficients of $dZ/dt$ based on a fiducial filter, $f_A(k)$.

39. A method of providing treatment to a living subject, comprising:

disposing a plurality of electrodes with respect to the thoracic cavity of said subject;

measuring at least one impedance waveform via at least one of said plurality of electrodes;

measuring at least one ECG waveform via at least one of said plurality of electrodes;

determining the stroke volume of the subject's heart using at least one discrete wavelet transform; and providing treatment to the subject based on the determined cardiac stroke volume.

40. The method of claim 39, wherein the act of determining stroke volume comprises:

(i) detecting one or more fiducial points within said at least one impedance waveform using wavelet transforms; and (ii) detecting one or more QRS complexes within said at least one ECG waveform.

41. The method of claim 40, wherein the act of determining stroke volume further comprises detecting one or more fiducial points within said at least one ECG waveform.

42. The method of claim 40, wherein the act of detecting one or more QRS complexes comprises detecting said one or more QRS complexes using a Haar wavelet transform.

43. A method of assessing cardiac output within a living subject, comprising the steps of:

disposing a plurality of electrodes disposed relative to the thoracic cavity of said subject for detecting electrical signals therefrom;

passing an electrical current through at least a portion of said thoracic cavity to permit measurement of at least one impedance waveform associated therewith;

measuring said at least one impedance waveform;

processing said at least one impedance waveform using discrete wavelet transforms for identification one or more fiducial points within said at least one impedance waveform; and determining cardiac output based at least in part on said one or more fiducial points.

44. A method of filtering a cardiac impedance (Z) waveform having a plurality of cardiac beats, comprising:

selecting a beat average;

calculating a first value of at least one parameter associated with said impedance waveform;

buffering said first value in at least one median filter, said at least one median filter being adapted to permit shifting with each successive one of said plurality of beats;

calculating a second value of at least one parameter associated with said impedance waveform;

buffering said second value in said at least one median filter; and calculating a median value for said at least one parameter based at least in part on said first and second values and said beat average.

45. Apparatus useful for assessing at least one hemodynamic parameter associated with a living subject comprising;

at least one electrical pathway adapted for signal communication with a monitoring system, said monitoring system comprising;
a plurality of electrodes adapted for use proximate the thoracic cavity of said living subject; and
a current source adapted to provide an electrical current through at least a portion of said thoracic cavity via at least a first of said plurality of electrodes, and produce an impedance waveform relating thereto on at least a second of said plurality of electrodes, wherein said at least second electrode of said plurality is in signal communication with said at least one electrical pathway; and a signal processing apparatus, operatively coupled to said at least one electrical pathway, said signal processing apparatus adapted to analyze said impedance waveform using wavelet transforms to assess said at least one hemodynamic parameter.

46. The apparatus of claim 45, wherein said monitoring system comprises an ECG monitor.

* * * * *